(12) United States Patent
Seppi et al.

(10) Patent No.: US 7,869,862 B2
(45) Date of Patent: Jan. 11, 2011

(54) SYSTEMS AND METHODS FOR FUNCTIONAL IMAGING USING CONTRAST-ENHANCED MULTIPLE-ENERGY COMPUTED TOMOGRAPHY

(75) Inventors: Edward J. Seppi, Portola Valley, CA (US); Larry Partain, Los Altos, CA (US); Michael Green, Palo Alto, CA (US); Gary Virshup, Cupertino, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 1344 days.

(21) Appl. No.: 10/687,522

(22) Filed: Oct. 15, 2003

(65) Prior Publication Data

US 2005/0084060 A1 Apr. 21, 2005

(51) Int. Cl.
*A61B 6/00* (2006.01)
(52) U.S. Cl. .................. 600/431; 600/420; 600/436
(58) Field of Classification Search .............. 600/407, 600/431, 420, 436; 378/145; 382/128, 130
See application file for complete search history.

(56) References Cited

U.S. PATENT DOCUMENTS

| | | | |
|---|---|---|---|
| 3,610,984 A | 10/1971 | Seki et al. | |
| 3,801,785 A * | 4/1974 | Barrett | 378/2 |
| 3,854,049 A | 12/1974 | Mistretta et al. | |
| 3,974,386 A * | 8/1976 | Mistretta et al. | 378/98.11 |
| 4,048,496 A | 9/1977 | Albert | |
| 4,247,774 A | 1/1981 | Brooks | |
| 4,432,370 A * | 2/1984 | Hughes et al. | 600/431 |
| 4,433,431 A | 2/1984 | Pfeiler | |
| 4,478,816 A * | 10/1984 | Ledley et al. | 424/9.42 |
| 4,482,918 A * | 11/1984 | Keyes et al. | 378/98.11 |
| 4,511,799 A | 4/1985 | Bjorkholm | |
| 4,731,807 A | 3/1988 | Plessis et al. | |
| 4,736,398 A * | 4/1988 | Graeff et al. | 378/98.3 |
| 4,859,849 A | 8/1989 | Shimura et al. | |

(Continued)

FOREIGN PATENT DOCUMENTS

EP 1016881 A2 7/2000

(Continued)

OTHER PUBLICATIONS

Robar, James L., et al., "Tumour Dose Enhancement Using Modified Megavoltage Photon Beams and Contrast Media," Phys. Med. Biol. 47 Institute of Physics Publishing, 2002, pp. 1-17, IOP Publishing Ltd., United Kingdom.

(Continued)

*Primary Examiner*—Brian Casler
*Assistant Examiner*—James Kish
(74) *Attorney, Agent, or Firm*—Vista IP Law Group, LLP.

(57) ABSTRACT

A method of generating images of a portion of a body includes introducing a contrast agent into the body, generating a first set of image data using radiation at a first energy level after the contrast agent is introduced into the body, generating a second set of image data using radiation at a second energy level after the contrast agent is introduced into the body, and creating a volumetric composite image using the first and the second sets of image data.

56 Claims, 14 Drawing Sheets

U.S. PATENT DOCUMENTS

| | | | |
|---|---|---|---|
| 4,890,310 A * | 12/1989 | Umetani et al. | 378/82 |
| 4,933,960 A | 6/1990 | Fujisaki | |
| 4,945,552 A * | 7/1990 | Ueda et al. | 378/98.11 |
| 5,138,167 A | 8/1992 | Barnes | |
| 5,293,416 A | 3/1994 | Pfeiler et al. | |
| 5,293,417 A | 3/1994 | Wei et al. | |
| 5,446,548 A | 8/1995 | Gerig et al. | |
| 5,533,080 A * | 7/1996 | Pelc | 378/5 |
| 5,570,403 A | 10/1996 | Yamazaki et al. | |
| 5,629,968 A * | 5/1997 | Trauernicht | 378/98.8 |
| 5,757,878 A | 5/1998 | Dobbs et al. | |
| 5,841,833 A | 11/1998 | Mazess et al. | |
| 5,864,146 A | 1/1999 | Karellas | |
| RE36,162 E | 3/1999 | Bisek et al. | |
| 6,278,760 B1 * | 8/2001 | Ogawa et al. | 378/5 |
| 6,333,991 B1 | 12/2001 | Schreiber et al. | |
| 6,418,193 B1 | 7/2002 | Albagli | |
| 6,445,765 B1 | 9/2002 | Frank et al. | |
| 6,473,634 B1 | 10/2002 | Barni | |
| 6,487,274 B2 | 11/2002 | Bertsche | |
| 6,614,878 B2 | 9/2003 | Bogatu et al. | |
| 6,683,934 B1 | 1/2004 | Zhao et al. | |
| 6,707,876 B2 | 3/2004 | Tanigawa | |
| 6,745,066 B1 * | 6/2004 | Lin et al. | 600/425 |
| 6,800,858 B1 | 10/2004 | Seppi | |
| 6,888,919 B2 | 5/2005 | Graf | |
| 6,922,462 B2 * | 7/2005 | Acharya et al. | 378/98.11 |
| 6,923,950 B2 * | 8/2005 | Salb | 424/9.1 |
| 6,937,696 B1 | 8/2005 | Mostafavi | |
| 6,950,493 B2 | 9/2005 | Besson | |
| 7,010,092 B2 | 3/2006 | Winsor | |
| 7,050,529 B2 | 5/2006 | Hoffman | |
| 7,054,410 B2 | 5/2006 | Zentai et al. | |
| 7,078,699 B2 | 7/2006 | Seppi | |
| 7,095,028 B2 | 8/2006 | Mollov et al. | |
| 7,289,599 B2 | 10/2007 | Seppi et al. | |
| 2002/0191751 A1 | 12/2002 | Bogatu et al. | |
| 2004/0057556 A1 | 3/2004 | Luhta et al. | |
| 2004/0114718 A1 | 6/2004 | Brown | |
| 2004/0116804 A1 | 6/2004 | Mostafavi | |
| 2004/0174959 A1 | 9/2004 | Green | |
| 2004/0195512 A1 | 10/2004 | Crosetto | |
| 2004/0247082 A1 | 12/2004 | Hoffman | |
| 2005/0084060 A1 | 4/2005 | Seppi et al. | |
| 2005/0084073 A1 | 4/2005 | Seppi et al. | |

FOREIGN PATENT DOCUMENTS

| | | |
|---|---|---|
| JP | 05036368 | 12/1993 |

OTHER PUBLICATIONS

International Search Report and Written Opinion for PCT/US04/34107 dated Jan. 14, 2008.
United States Patent and Trademark Office Action dated Mar. 18, 2008 for U.S. Appl. No. 10/687,550.
Office Action dated Dec. 22, 2008 for U.S. Appl. No. 10/687,573.
Office Action dated Jul. 31, 2008 for U.S. Appl. No. 10/687,573.
Office Action dated Mar. 13, 2008 for U.S. Appl. No. 10/687,573.
Office Action dated Nov. 20, 2007 for U.S. Appl. No. 10/687,573.
Office Action dated Feb. 8, 2007 for U.S. Appl. No. 10/687,573.
Office Action dated Sep. 26, 2006 for U.S. Appl. No. 10/687,573.
Office Action dated May 30, 2006 for U.S. Appl. No. 10/687,573.
Office Action dated Mar. 7, 2006 for U.S. Appl. No. 10/687,573.
Office Action dated Jun. 10, 2005 for U.S. Appl. No. 10/687,573.
Advisory Action dated Apr. 3, 2009 for U.S. Appl. No. 10/687,573.
Advisory Action dated Mar. 4, 2009 for U.S. Appl. No. 10/687,573.
Advisory Action dated Apr. 19, 2007 for U.S. Appl. No. 10/687,573.
Office Action dated Oct. 30, 2008 for U.S. Appl. No. 10/687,550.
Office Action dated Mar. 18, 2008 for U.S. Appl. No. 10/687,550.
Office Action dated Aug. 21, 2007 for U.S. Appl. No. 10/687,550.
Office Action dated Jan. 3, 2007 for U.S. Appl. No. 10/687,550.
Office Action dated Jun. 15, 2006 for U.S. Appl. No. 10/687,550.
Office Action dated Nov. 16, 2005 for U.S. Appl. No. 10/687,550.
Advisory Action dated Feb. 19, 2009 for U.S. Appl. No. 10/687,550.
Advisory Action dated Jan. 9, 2008 for U.S. Appl. No. 10/687,550.
Non-Final Office Action dated Dec. 28, 2009 for U.S. Appl. No. 10/687,550.
Notice of Allowance dated Sep. 2, 2009 for U.S. Appl. No. 10/687,573.
Final Office Action dated Jul. 7, 2010 for U.S. Appl. No. 10/687,550.
Non-Final Office Action dated Nov. 12, 2010 for U.S. Appl. No. 12/684,069.

* cited by examiner

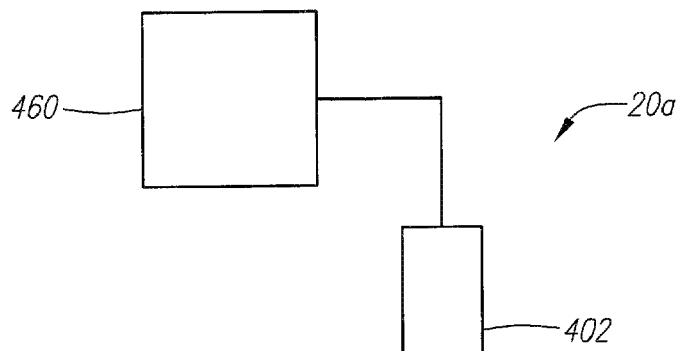
FIG. 4A
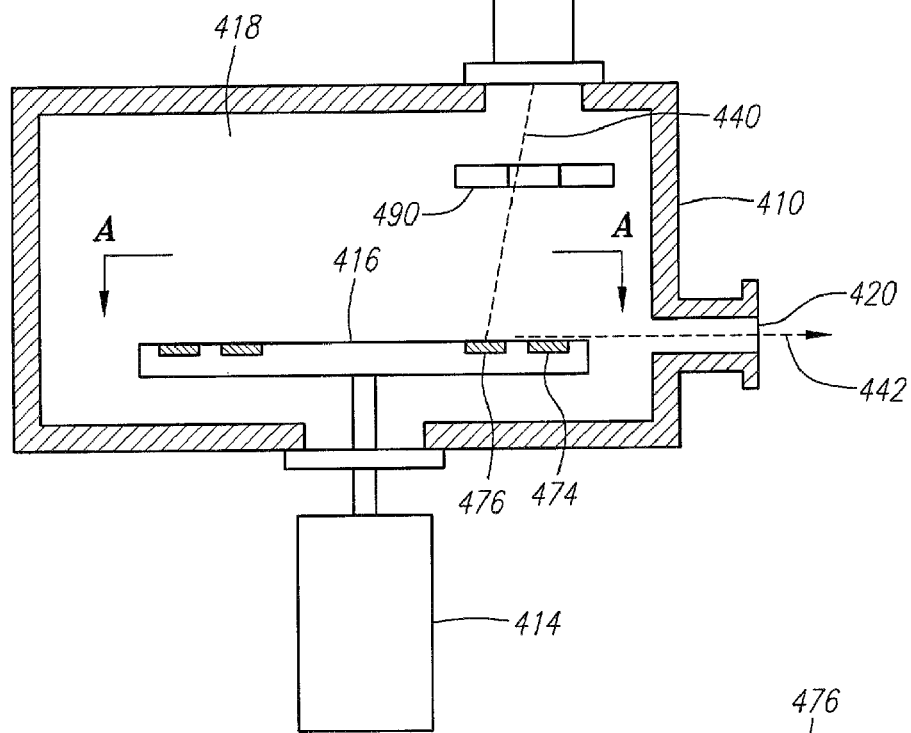
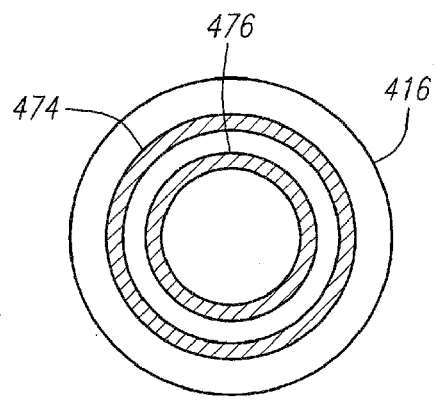
Section A-A

Section B-B

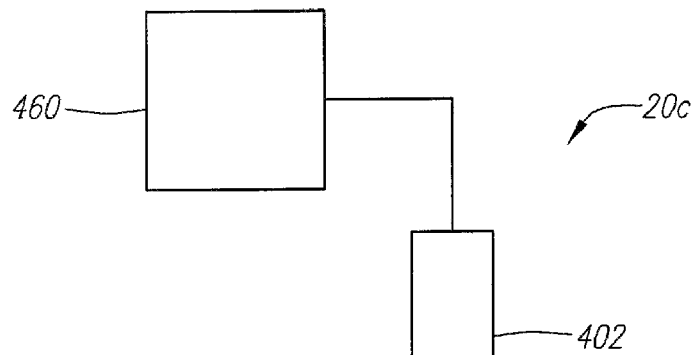
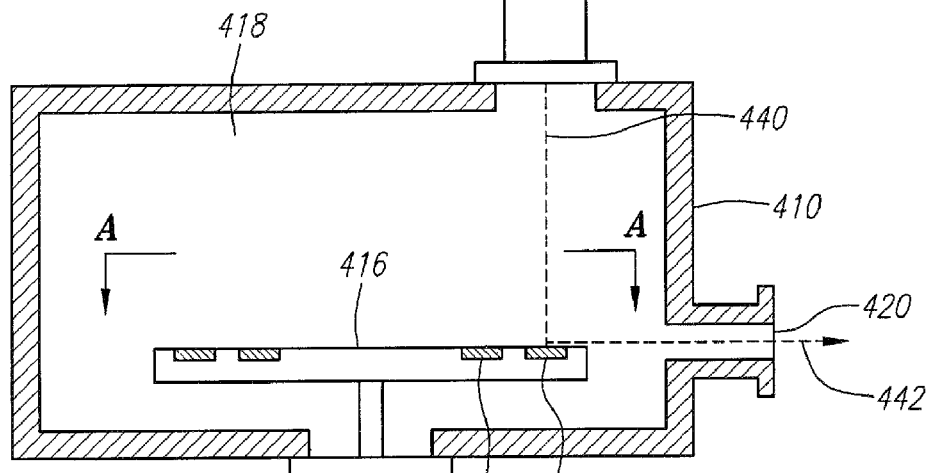
FIG. 4C
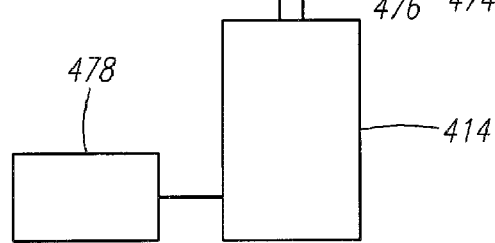
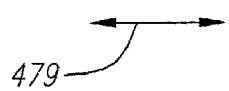
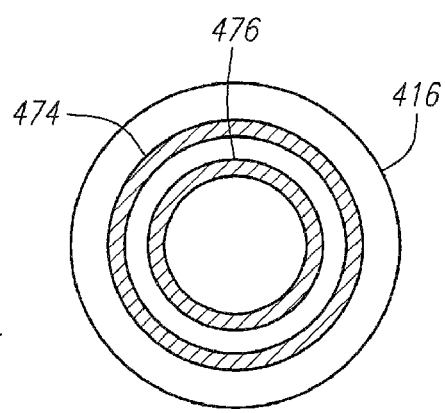
Section A-A

SYSTEMS AND METHODS FOR FUNCTIONAL IMAGING USING CONTRAST-ENHANCED MULTIPLE-ENERGY COMPUTED TOMOGRAPHY

BACKGROUND OF THE INVENTION

1. Field of the Invention

This invention relates generally to systems and methods for image acquisition and, more specifically, to systems and methods for angiogenesis imaging using computed tomography.

2. Background of the Invention

Each year, many women are diagnosed with breast cancer, and the number of deaths associated with breast cancer has reached 40,000 per year. The death toll cannot be substantially reduced because current screening and diagnostic techniques do not detect all cancers at an early enough stage to effectuate a treatment cure. As such, early diagnosis and treatment of breast cancer is highly desirable.

Tumors larger than a few millimeters in cross section generally require a blood supply in order to obtain nutrients and oxygen for growth. Vessels that grow around the tumors proliferate in a disorganized manner and they may leak and pool blood around the tumors. Iodine-contrast-enhanced mammography has been used to detect tumors in women's breasts. In such procedure, contrast agent is introduced into a patient's vessel, and mammograms of the patient's breast are obtained before and after the contrast injection. By digitally subtracting the pre-injection image from post-injection images that are obtained over a time period of 1 to 7 minutes, a composite image can be obtained that shows tumor blood supply and "pooling" in the vicinity of the tumor. However, the contrast resolution of mammography is usually limited, and malignancies in tissues that are below 5 millimeters in cross-sectional dimension may not be detectable.

In order to create the composite image, the post-injection images obtained over the prescribed time period need to have a same image registration with the pre-injection image such that a pixel in the post-injection images can be processed with a corresponding pixel in the pre-injection image. Sometimes, a portion of the patient being imaged may move, e.g., translates 1 to 400 microns and/or rotates 1 to 2 degrees, when between images are taken. In such cases, a physician would need to realign the two images. If the pre-injection image and the post-injection images cannot be realigned or registered, the image collection procedure will need to be repeated. Usually, in a mammography procedure, a patient's breast is compressed by a set of paddles to reduce movements of the breast while pre-injection and post-injection images are obtained. However, patients usually experience discomfort from compression of the breasts. The discomfort can become so severe that the imaging procedure is terminated. In addition, the use of paddles to compress breast tissue restrict blood flow into the breast, thereby limiting an amount of contrast agent that can be delivered into the breast. This in turn, interferes with the kinetics of the contrast agent, and makes angiogenesis imaging difficult.

For the foregoing, improved systems and methods for imaging angiogenesis are desirable.

SUMMARY OF THE INVENTION

In accordance with an embodiment of the invention, a method of generating images of a portion of a body includes introducing a contrast agent into the body, generating a first set of image data using radiation at a first energy level after the contrast agent is introduced into the body, generating a second set of image data using radiation at a second energy level after the contrast agent is introduced into the body, and creating a composite image using the first and the second sets of image data. In one embodiment, the first energy level is below a k-edge of the contrast agent, and the second energy level is above a k-edge of the contrast agent. In one embodiment, the composite image is created by subtracting a logarithmic transform of the first set of image data from a logarithmic transform of the second set of image data. Such technique results in tissue features being removed from the image while features attributable to the introduced contrast agent are retained in the image.

In accordance with another embodiment of the invention, a system for generating CT image data using radiation at a plurality of levels is provided. The system includes a gantry, a x-ray source assembly secured to the gantry, and a detector assembly. By means of non-limiting examples, the x-ray source assembly can include a plurality of voltage supplies, a plurality of target materials (anodes), and/or a plurality of filters, thereby allowing the x-ray source assembly to deliver radiation having different characteristics. The detector assembly can include a single imager for generating image data in response to radiation at different energy levels. Alternatively, the detector assembly can include a plurality of imagers, each of which configured to generate image data in response to radiation at a prescribed range of energy levels. By means of non-limiting examples, the imager can include a scintillating material that converts x-ray into light, or a photoconductor layer that produces electron-hole-pairs in response to x-ray radiation. In some embodiments, the imager can include a plurality of first imaging elements having a first radiation detection characteristic; and a plurality of second imaging elements having a second radiation detection characteristic.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how advantages and objects of the present invention are obtained, a more particular description of the present invention briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 4A-4F illustrate x-ray source assemblies in accordance with different embodiments of the invention;

DETAILED DESCRIPTION OF THE PREFERRED EMBODIMENTS

Figure 1:
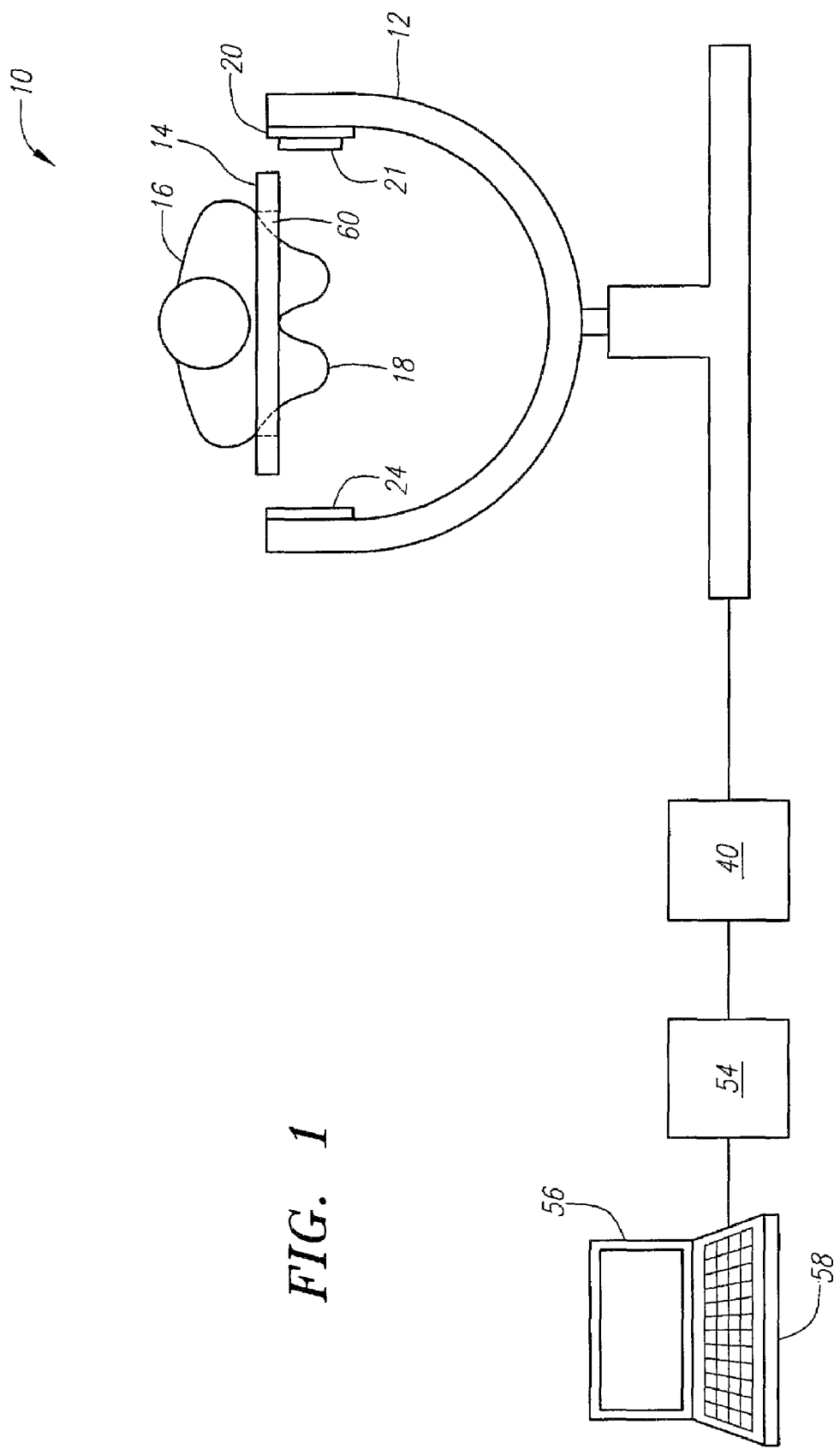
FIG. 1 illustrates a computed tomography system in which embodiments of the present invention may be implemented.

Various embodiments of the present invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. In addition, an aspect or a feature described in conjunction with a particular embodiment of the present invention is not necessarily limited to that embodiment and can be practiced in any other embodiments of the present invention.

Referring now to the drawings, in which similar or corresponding parts are identified with the same reference numeral, FIG. 1 illustrates a computed tomography (CT) image acquisition system 10 in accordance with some embodiments of the present invention. The system 10 includes a gantry 12, and a panel 14 for supporting a patient 16. The gantry 12 includes a x-ray source assembly 20 that projects a beam of x-rays, such as a fan beam or a cone beam, towards a detector assembly 24 on an opposite side of the gantry 12 while a portion of the patient 16 is positioned between the x-ray source assembly 20 and the detector assembly 24. In the illustrated embodiment, the x-ray source assembly 20 is configured to deliver radiation at a plurality of energy levels, and the detector assembly 24 is configured to generate image data in response to radiation at different energy levels. The x-ray source assembly 20 may include a collimator 21 for adjusting a shape of the x-ray beam. In some embodiments, the collimator 21 includes one or more filters (not shown) for creating radiation with certain prescribed characteristics. The detector assembly 24 has a plurality of sensor elements configured for sensing a x-ray that passes through the patient 16. Each sensor element generates an electrical signal representative of an intensity of the x-ray beam as it passes through the patient 16.

Figure 1A:
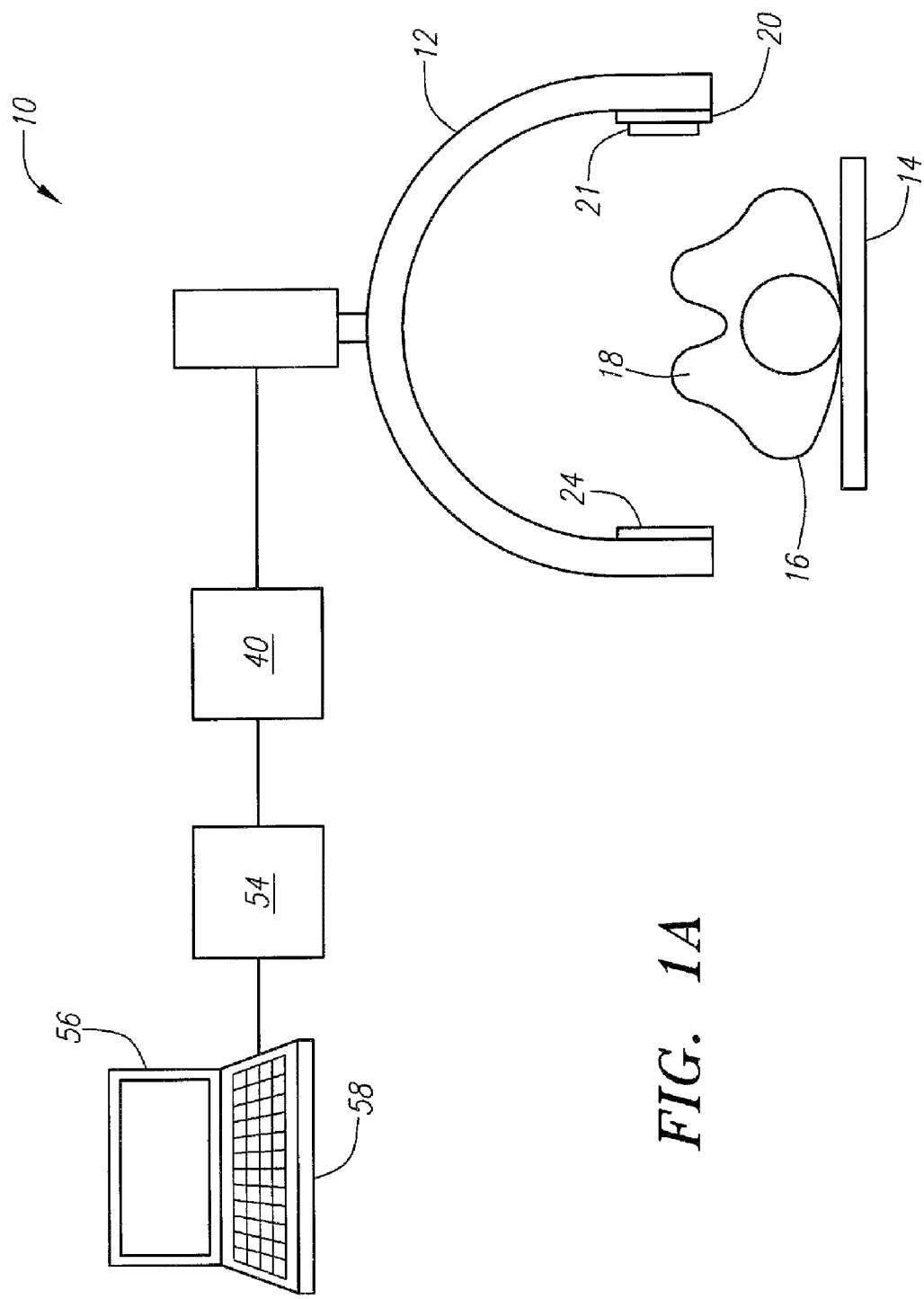
FIGS. 1A and 1B illustrate variations of the computed tomography system of FIG. 1.
Figure 1B:
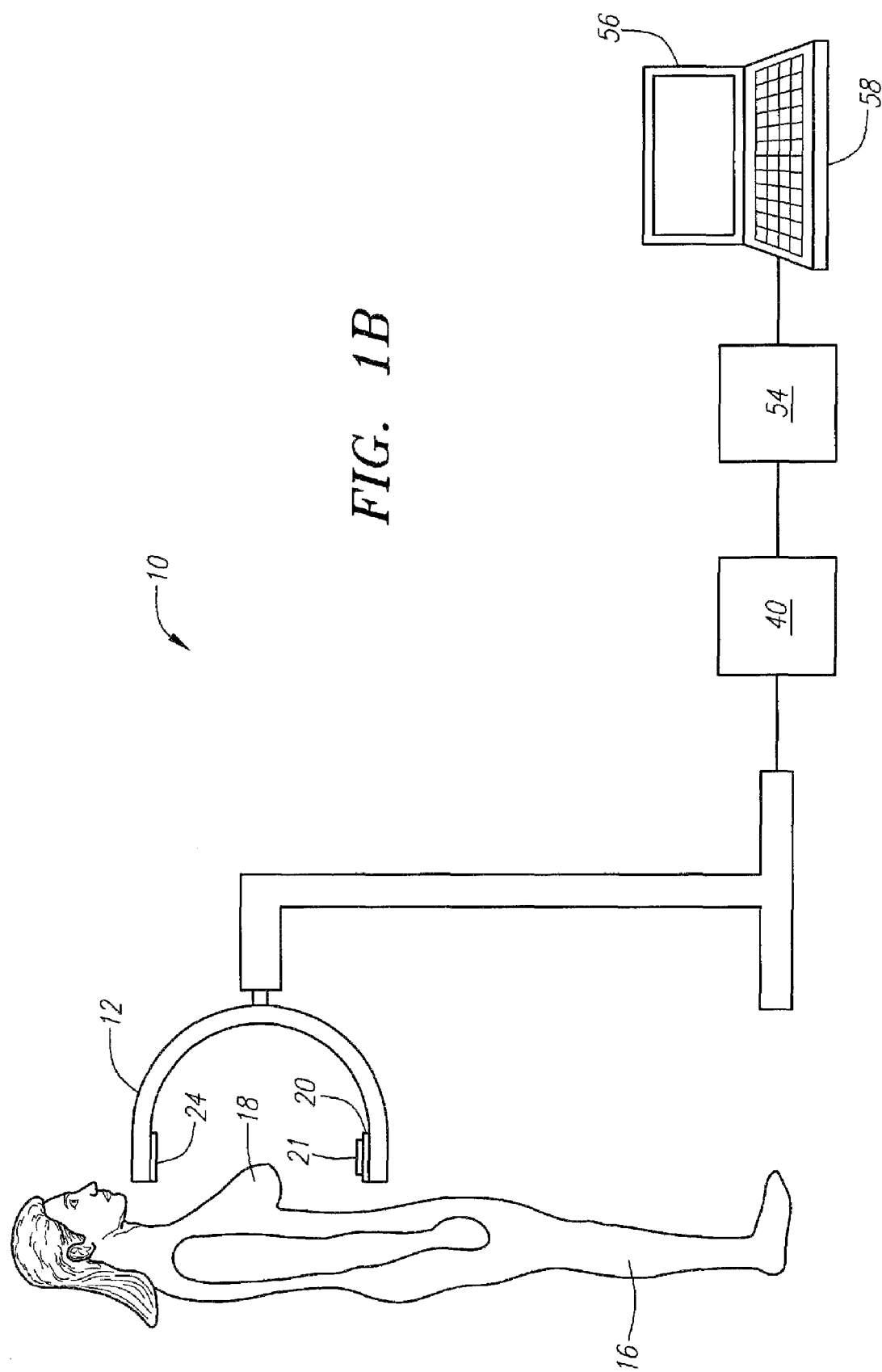

In the illustrated embodiment, the panel 14 has an opening 60 through which a breast 18 of the patient 16 can be placed when the patient 16 is lying on the panel 14 facing downward. Such arrangement allows the breast 18 to be placed between the x-ray source assembly 20 and the detector assembly 24. In an alternative embodiment, the panel 14 can be used to support the patient 16 facing upward (FIG. 1A). In such case, the gantry 12 is placed above the panel 14, and is configured to rotate about the breast 18. In another embodiment, the gantry 12 is configured to rotate about the breast 18 while the patient 16 is standing (or sitting) in an upright position (FIG. 1B). It should be noted that the positioning of the gantry 12 should not be limited to the examples illustrated previously, and that the gantry 12 can have other configurations (e.g., positions or orientations of an axis of rotation), depending on a position of the panel 14, and a position and orientation of an object for which imaging is desired.

In the illustrated embodiment, the CT image acquisition system 10 also includes a processor 54, a monitor 56 for displaying data, and an input device 58, such as a keyboard or a mouse, for inputting data. The processor 54 is coupled to a control 40. The rotation of the gantry 12 and the operation of the x-ray source assembly 20 are controlled by the control 40, which provides power and timing signals to the x-ray source assembly 20 and controls a rotational speed and position of the gantry 12 based on signals received from the processor 54. The control 40 also controls an operation of the detector assembly 24. For example, the control 40 can control a timing of when image signal/data are read out from the detector assembly 24, and/or a manner (e.g., by rows or columns) in which image signal/data are read out from the detector assembly 24. Although the control 40 is shown as a separate component from the gantry 12 and the processor 54, in alternative embodiments, the control 40 can be a part of the gantry 12 or the processor 54.

During a scan to acquire x-ray projection data (i.e., CT image data), the x-ray source assembly 20 projects a beam of x-rays towards the detector assembly 24 on an opposite side of the gantry 12, while the gantry 12 rotates about the breast 18. In one embodiment, the gantry 12 makes a 360° rotation around the breast 18 during image data acquisition. Alternatively, if a full cone detector is used, the system 10 may acquire data while the gantry 12 rotates 180° plus the angle of the beam pattern. Other angles of rotation may also be used, depending on the particular system being employed. In one embodiment, the detector assembly 24 is configured to generate at least 900 frames of images in less than 1 second. In such case, the gantry 12 only needs to rotate around the breast 18 once in order to collect sufficient amount of image data for reconstruction of computed tomography images. In other embodiments, the detector 24 may be configured to generate frames at other speeds.

Figure 2:
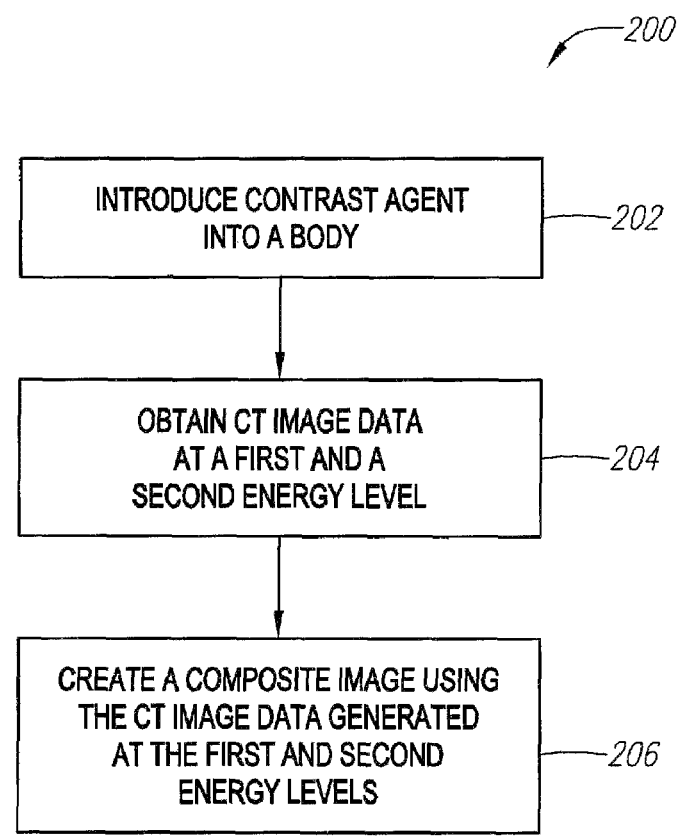
FIG. 2 is a flow chart illustrating a method for imaging angiogenesis in a tissue.

FIG. 2 is a flowchart 200 illustrating a method for imaging angiogenesis in the breast 18 using the system 10. First, a contrast agent is introduced inside the patient's body, and more specifically, into a vascular system of the patient 16 (Step 202). The contrast agent can be administered with a mechanical power injector via an intravenous catheter that is placed in antecubital or forearm vein, at a rate between 2 to 6 milliliter (mL) per second. In the illustrated embodiment, about 50 to 70 mL of contrast agent is administered to the patient 16. However, other amounts of contrast agent can be introduced inside the patient's body, depending on a patient's size, and/or a requirement of a particular procedure.

A variety of contrast agent can be administered to the patient 16. In the illustrated embodiment, the contrast agent includes iodine, which has a k-absorption edge (K-edge) of 33 keV. Alternatively, gadolinium (Gd) (having a k-edge of 50.2 keV) chelated with diethylenetriaminepentaacetic acid (DTPA) can be used. Gd-DTPA is well tolerated by humans, and no serious side effects have been reported. The contrast agent can also include materials, such as holmium (having a k-edge of 56 keV), erbium (having a k-edge of 58 keV), lanthanum, cerium, praseodymium, neodymium, samarium, europium, terbium, dysprosium, thulium, ytterbium, lutetium (having a k-edge of 63.3 keV), and other rare earth elements. Compounds, DTPA complexes, ethylenediamine tetraacetic acid (EDTA) complexes, nitrilotriacetic acid (NTA) complexes, and other chelate compounds, formed from any of the above mentioned elements can also be used. Elements with atomic numbers higher than that of gadolinium is particularly suitable for the contrast agent because x-ray absorption of body tissue would be lower at higher x-ray photon energies. However, elements with atomic numbers lower than that of gadolinium can also be used, depending on a particular k-edge requirement of an application. K-edge energies for various materials are known. Other soluble, non-toxic, chelate compounds can also be used. In addition, noble gases such as Xenon, and agents composed of stable isotopes of radio nuclides such as Ti, Yb, Cs, Xe, I, In, and Tc.

Next, the patient 16 is positioned such that the breast 18 of the patient 16 is positioned between the x-ray source assembly 20 and the detector assembly 24. After a prescribed time (e.g., 150 seconds) measured from the point of contrast injection has lapsed, the gantry 12 then rotates about the breast 18 to generate two sets of image data (Step 204). In the illustrated embodiment, the two sets of image data are generated in quick succession (e.g., within 5 to 20 milliseconds) using radiation at different levels. It should be noted that the time within which the first and the second sets of image data are generated should not be limited to the example, and that the first and the second sets of image data can be generated within any time period as long as the first and the second sets of image data are captured fast enough to render the object being imaged appear motionless. As the gantry 12 rotates about the breast 18, the x-ray source assembly 20 alternately emits radiation at a first and a second energy levels. Particularly, the radiation should have a first energy level that is below a k-absorption edge (K-edge) of the contrast agent, and a second energy level that is above the k-edge of the contrast agent. The emitted radiation at both levels is attenuated by the breast 18 and impinges on the detector assembly 24. The detector assembly 24, in turn, generates the first and the second sets of image data in response to radiation at the first and second levels, respectively. Additional sets of image data for different gantry angle can be generated as the gantry 12 rotates about the breast. After a desired number of sets of image data (e.g., sufficient for reconstruction of volumetric image) have been generated, the image data can be stored in a computer readable medium for later processing. In some embodiments, the gantry 12 makes at least one rotation to generate the sets of image data. In alternative embodiments, the gantry 12 makes a partial rotation to generate the sets of image data.

In alternative embodiments, instead of acquiring the first and the second sets of image data during a gantry rotation, the first set of image data can be generated during a first rotation (or rotations), and the second set of image data can be generated during a successive rotation (or rotations). In such case, the patient 16 can be instructed to hold breath while the gantry 12 is rotating about the breast 18 to collect image data. This ensures or increases the chance that an object captured at a position in the first set of image data will also be captured at substantially the same position in the second set of image data. For example, to increase the chance that the image data taken at the first and the second energy levels will have similar spatial registration, the image data are taken at the end of an expiration with breath holding. In other embodiments, a patient position monitoring system can be employed to monitor positions of the patient 16 as the gantry 12 is rotating about the breast 18. In such case, motion signal representative of a physiological movement of the patient 16 can be used to predictively gate an operation of the x-ray source assembly 20 such that image data can be generated at prescribed phase(s) or prescribed amplitude range(s) of a physiological cycle. In other embodiments, the motion signal can be synchronized with the image data to a common time base, and CT volumetric images can be retrospectively constructed using the image data. Patient position monitoring systems, and systems and methods for predictive gating have been described in U.S. patent application Ser. No. 09/893,122, filed Jun. 26, 2001, the entire disclosure of which is hereby incorporated by reference.

After the image data for both radiation levels have been obtained, the image data are then processed to create a composite image (Step 206). In some embodiments, image data generated using radiation at the first and second energy levels are used to construct a first volumetric image and a second volumetric image, respectively. Various techniques can be used to construct a volumetric image. Construction of volumetric images using cone beam CT has been described in U.S. patent application Ser. No. 10/656,438, entitled "Radiation process and apparatus", filed Sep. 5, 2003, which claims priority to U.S. Provisional Patent Application Ser. No. 60/416,022, the disclosures of which are expressly incorporated by reference herein. After the first and the second volumetric images are constructed, they are processed to obtain the composite image. For example, the first volumetric image can be digitally subtracted from the second volumetric image to obtain a composite image. Alternatively, a logarithmic transform is applied to the first and the second volumetric images, which converts values assigned to each pixel of the first and the second volumetric image to a natural logarithm of the original value. The first transformed image are then digitally subtracted from the second transformed image to obtain a composite image. Such technique removes much of the dependence on the background breast thickness and an intensity of the x-ray exposure used from the subtracted image. Different scaling factors can also be applied to the first and the second volumetric images before the first volumetric image is subtracted from the second volumetric image. Other frame processing algorithms and techniques can also be used to create the composite image. For example, a boxcar filter can be applied to the first and the second volumetric images for noise reduction, as is known in the art. In alternative embodiments, instead of creating the first and the second volumetric images, the first image data and the second image data can be processed to obtain composite image data, and the composite image data are then used to construct the composite image.

Various methods can be used to align the first image data with the second image data to create the composite image. In some embodiments, the first and the second image data are generated at the same gantry angles. For example, for the case in which the first and the second sets of image data are generated within a gantry rotation, the gantry 12 can stop rotating as the first and the second sets of image data are being generated at a gantry angle. The gantry 12 then rotates to a next position to generate next sets of image data. In such case, since the first and the second sets of image data are generated at the same gantry angles, the first and the second volumetric images generated from the first and the second image data, respectively, would be automatically aligned with each other. For the case in which the first and the second sets of image data are each generated at successive gantry rotations, the second image data can be generated (in a subsequent gantry rotation) at the same gantry angles at which the first image data are generated during a previous gantry rotation. In such case, since the first and the second sets of image data are also generated at the same gantry angles, the first and the second volumetric images generated from the first and the second image data, respectively, would be automatically aligned with each other.

In other embodiments, the first and the second image data are generated at different gantry angles. In such cases, the first image data and the second image data are used to create a first volumetric image and a second volumetric image, respectively. The first volumetric image can then be aligned with the second volumetric image by translating and/or rotating either of the first and the second volumetric images relative to the other, such that a feature in the first volumetric image matches with the same feature in the second volumetric image. Alternatively, an average shift in the gantry angle between the first image data and the second image data can be determined, and the average shift in the gantry angle can be used to align the first and the second volumetric images. In some embodiments, the average shift in the gantry angle between the first and second image data can also be taken into account when constructing either or both of the first and the second volumetric images such that the first and the second volumetric images are aligned. In other embodiments, the first image data can be modified to align with the second image data. For example, if first image data are generated at gantry angles=15° and 25° (measured from an arbitrary reference) using radiation at the first energy level, and second image data are generated at gantry angle=20° using radiation at the second energy level, then the first image data generated at gantry angles 15° and 25° can be processed (e.g., averaged, or interpolated) to obtain modified first image data that correspond to a gantry angle of 20°. A preferred method for accomplishing this interpolation is to use known techniques for interpolation. For example, for band limited data, Fourier analysis techniques can be used to determine an exact interpolation. The modified first image data and the second image data can then be used to generate a first volumetric image and a second volumetric image, respectively. In some embodiments, the shift in a gantry angle between the first image data (taken at first energy level) and the second image data (taken at second energy level) is selected to be small compared to a change in gantry angle between each image data that are taken at the same energy level. Such technique will enhance image registration between the first volumetric image and the second volumetric image.

Figure 3A:
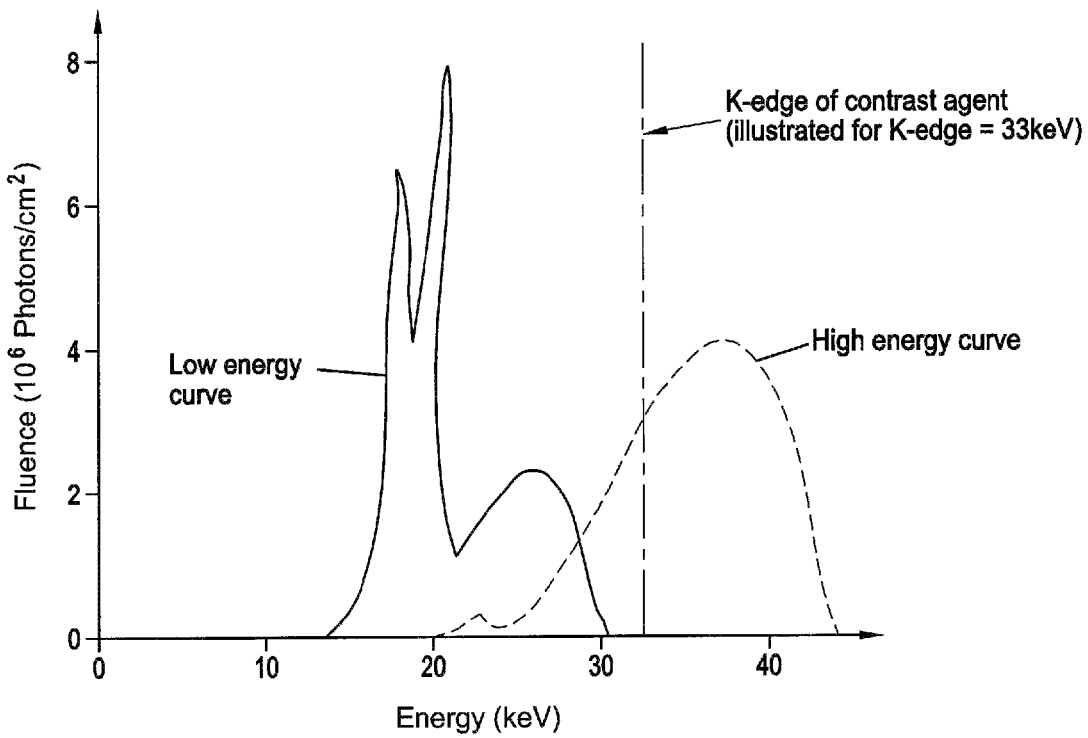
FIG. 3A is a graph showing a low energy spectrum curve, a high energy spectrum curve, and a k-absorption edge of a contrast agent.

Those skilled in the art understand that a contrast agent having a k-edge attenuates radiation above and near its k-edge, and does not substantially attenuate radiation below and near its k-edge. For example, Iodine, which has a k-edge of approximately 33 keV, attenuates radiation that is higher than about 33 keV, and does not substantially attenuate radiation below about 33 keV (FIG. 3A). As such, by performing frame subtraction of the two volumetric images (or variation of the two volumetric images), non-contrast features, i.e., images of object that does not contain contrast agent, are removed or reduced from the composite image, while contrast features, i.e., images of object that contains contrast agent, are enhanced. For example, subtraction of the first image from the second image will reduce an image contrast (make less visible) for bone and tissue that do not contain the contrast agent, and retain or enhance an image contrast (make more visible) of vessels that contain the contrast agent.

In some embodiments, the composite image can be used to identify cancerous tissue. Cancerous tissue or tumors may take up contrast agent faster and to a greater degree than do normal tissue because of the denser capillaries associated with tumor angiogenesis. As such, location of potential cancerous tissue can be determined by identifying any unusual concentration of the contrast agent represented in the composite image.

The above described imaging procedure has several advantages over the traditional mammography. First, the use of a CT system eliminates the need to perform breast compression, thereby eliminating any discomfort that may be experienced by the patient 16 due to breast compression, and allowing transport of contrast agent into the breast 18. In addition, the above described imaging procedure eliminates superimposition of structures within the breast 18, and provides better contrast and detail resolution than those obtained from traditional mammography.

In the above described embodiment, a single type of contrast agent is used. However, in alternative embodiments, a plurality of contrast agents can be used. In such cases, each of the contrast agents can be selected such that tissue having a particular characteristic or feature can be enhanced in a composite image. The plurality of contrast agents can be simultaneously injected into the patient 16, or alternatively, administered to the patient 16 at different prescribed times.

Furthermore, instead of generating image data using radiation at a first and a second energy levels, in alternative embodiments, image data can be generated using radiation at more than two energy levels. In such cases, the generated image data at different energy levels are processed to generate a composite image such that an appearance of a feature due to a contrast agent can be enhanced or maximized in the contrast image. For example, image data using radiation at one or more energy levels can be used to form a first set and a second set of integrated image data. Each of the first and second sets of integrated image data can be image data generated using radiation at one of the levels, or alternatively, can be created by integrating image data that have been generated using radiation at a plurality of energy levels. The first set of integrated data can then be subtracted from the second set of integrated image data to form a composite image, as similarly discussed previously.

In the above described embodiment, a volumetric composite image (or composite image data) is generated for a prescribed lapsed time after the injection of the contrast agent. However, in alternative embodiments, steps 204 and 206 can be repeated to generate additional volumetric composite images (or composite image data) for different lapsed time after the injection of the contrast agent. In such case, image data at the first and second radiation energy levels are generated at different lapsed time after injection of the contrast agent. Volumetric images (or composite image data) associated with the first and the second radiation energy levels can be constructed for each of the lapsed time using the image data, and the same technique described previously can be used to obtain a composite image for each of the lapsed times. In some embodiments, the volumetric composite images (or composite image data) for the different lapsed times can be used to determine time-resolved kinetics of the contrast agent. For example, features of an object within a region of interest in a composite image can be used to calculate an iodine concentration at a location of the object (i.e., target site). After iodine concentrations that correspond to different times at which image data are generated have been determined, the iodine concentration for a target site and for a normal tissue site can be plotted versus time, and the graph for the target site can be compared with the graph for the normal tissue site to determine whether the target site contains abnormal tissue. It is well known that kinetic curve for abnormal tissue can exhibit different characteristic from the kinetic curve for a normal tissue.

Figure 3B:
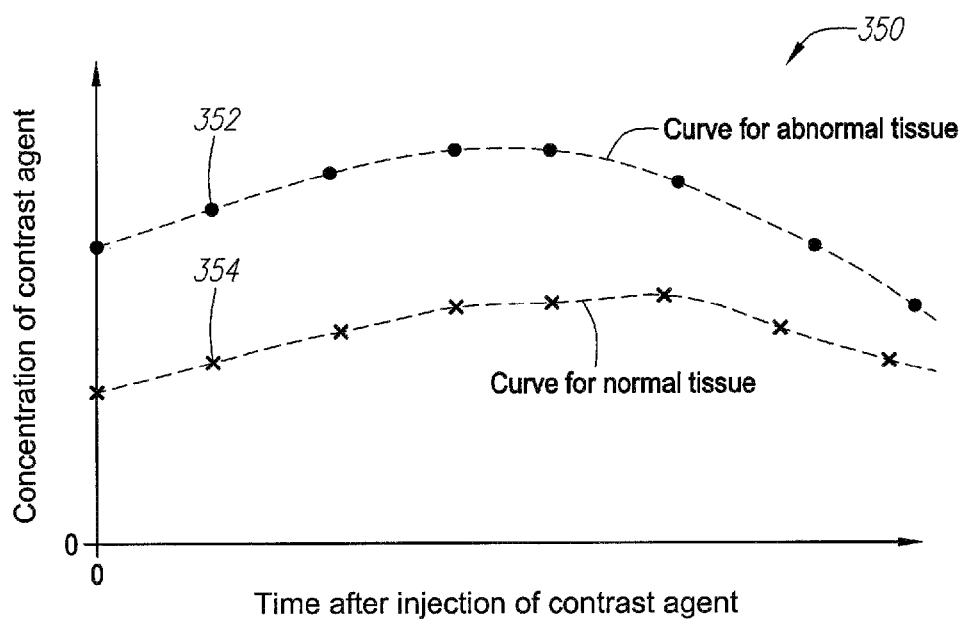
FIG. 3B is a graph showing how concentration of contrast agent varies over time for normal and abnormal tissue.

FIG. 3B is an example of a graph 350 that can be generated using the above described procedures. The graph 350 includes a first set of data points 352 representing concentration of the contrast agent at a target site that are generated at various times after the contrast agent has been injected into the patient 16. The graph 350 also includes a second set of data points 354 representing concentration of the contrast agent at a normal tissue region that are generated at various times after injection of the contrast agent. As shown in the graph 350, the data points 352, 354 show how concentration of the contrast agent increases (due to absorption of the contrast agent) and decreases (due to elimination of the contrast agent) over time, for the target site and the normal tissue, respectively. Concentration of the contrast agent for abnormal tissue, such as tumor tissue or cancerous tissue, may have a higher curve (or data points) due to additional vessel growths (angiogenesis) associated with the abnormal tissue.

X-ray Source Assembly

As previously discussed, the x-ray source assembly 20 is configured to generate radiation at a plurality of levels. The x-ray source assembly 20 can be variously constructed to perform such function. FIG. 4A shows a x-ray source assembly 20a in accordance with one embodiment of the invention. The x-ray source assembly 20a includes an electron gun 402 (cathode), and a voltage supply 460 secured to the electron gun 402. The voltage supply 460 is configured to supply a voltage to the electron gun 402 during use. The x-ray source assembly 20a also includes a tube 410 to which the electron gun 402 is secured, and a first target material 474 and a second target material 476 (anodes) located inside a lumen 418 of the tube 410. The target materials 474, 476 can include a variety of materials that have suitable mechanical, thermal, electronic properties, and other suitable properties for production of prescribed x-ray spectra and intensity. Examples of materials that can be used includes holmium, erbium, lanthanum, cerium, praseodymium, neodymium, samarium, europium, terbium, dysprosium, thulium, ytterbium, lutetium, barium, molybdenum, rhodium, zirconium, hafnium, tungsten, titanium, rhenium, rhenium, molybdenum, copper, graphite, other rare earth materials and platinum group metals, and combination thereof. Suitably stable and refractory compounds, such as cerium boride ($CeB_6$), and other compounds formed from any of the above mentioned materials can be used for the target materials 474, 476. In the illustrated embodiment, the target materials 474, 476 are secured to a disk 416, and are positioned relative to each other in a radial arrangement. The disk 416 is rotatably coupled to a motor 414. Alternatively, the disk 416 itself can be made from the target materials 474, 476. The target materials 474, 476 are substantially centered at an axis of rotation of the disk 416. Alternatively, either or both of the target materials 474, 476 can be off-centered from the axis of rotation of the disk 416. The x-ray source assembly 20a further includes an electron deflector 490 located within the lumen 418 of the tube 410. In the illustrated embodiment, the electron deflector 490 comprises an electromagnetic field generator that generates electromagnetic field, which changes a path of traveling electrons as they exit the electron gun 402. The electron deflector 490 is coupled to the processor 54 and/or the control 40, which controls an operation of the electron deflector 490.

During use, the voltage supply 460 supplies a voltage to the electron gun 402 to generate a cloud of electrons. Due to a potential that is generated between the electron gun 402 and the first target material 474, the electrons accelerate towards the first target material 474, forming a beam 440 of electrons. The beam 440 can be a continuous beam, or alternatively, a pulsed beam. X-rays at a first energy level are generated by the interaction of the electron beam 440 and the first target material 474. Most of the generated x-rays are confined by the tube 410, while a beam 442 of the x-rays escape from an x-ray window 420. As x-rays are generated, the motor 414 rotates the disk 416 such that the electron beam 440 impinges on different locations on the first target material 474, thereby cooling the first target material 474. To generate x-ray beam at a second energy level, the processor 54 modulates the electron deflector 490 such that the electron deflector 490 deflects exiting electrons from the electron gun 402 onto to the second target material 476. The deflected electrons impinge onto the second target material 476 and interact with the second target material 476 to generate radiation at the second energy level, as similarly discussed previously. In one embodiment, the first generated radiation has an energy level that is below a k-edge of a contrast agent, and the second generated radiation has an energy level that is higher than a k-edge of the contrast agent.

In alternative embodiments, instead of having an electromagnetic field generator, the electron deflector 490 can have other configurations. For example, the electron deflector 490 can include a structure for physically deflecting or selecting electrons emitted from the electron gun 402. In such case, the structure can be coupled to a positioner, which changes a position and/or orientation of the structure, thereby deflecting electrons towards different directions. Furthermore, in alternative embodiments, instead of having an electromagnetic field generator, the x-ray source assembly 20a can include a magnetic field generator that generates magnetic field for deflecting electrons that are accelerating towards either of the target materials 474, 476. It should be noted that the configuration (e.g., shapes, dimensions, designs, and arrangements of various components) of the x-ray source assembly 20a should not be limited to the example illustrated in the figure, and that the x-ray source assembly 20a can have other configurations. For example, in other embodiments, instead of securing the target materials 474, 476 to a rotatable disk 416, the target materials 474, 476 can be coupled to a reservoir of cooling fluid.

Figure 4B:
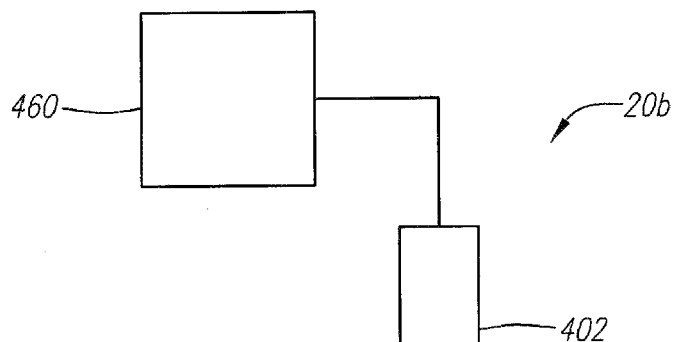
Figure 4B:
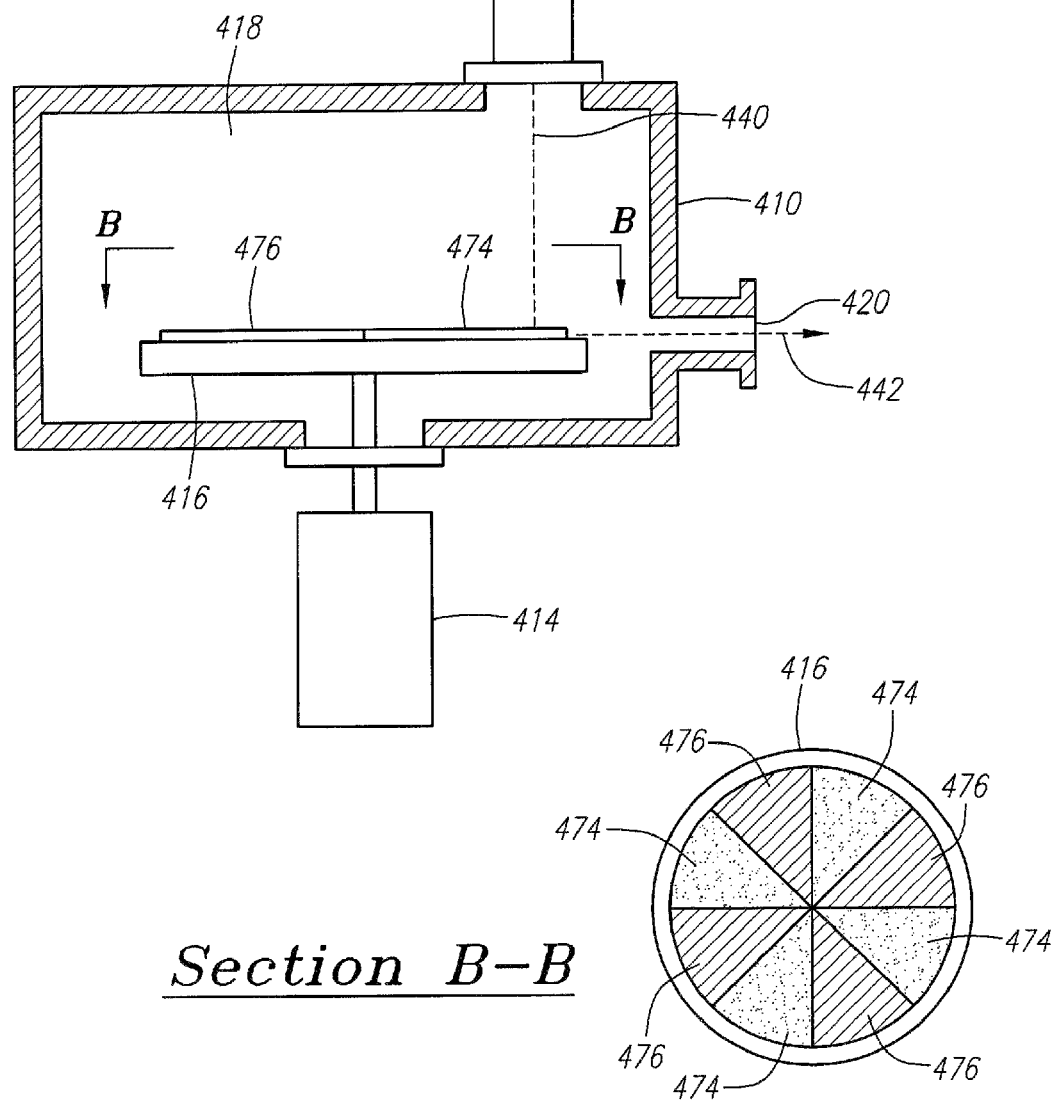

FIG. 4B shows another x-ray source assembly 20b in accordance with other embodiments of the invention. The x-ray source assembly 20b is similar to the x-ray source assembly 20a, except that it does not have the electron deflector 490. In the illustrated embodiment, the first and the second target materials 474, 476 are secured to the disk 416 relative to each other in a circumferential arrangement (Section B-B). The motor 414 is coupled to the processor 54 and/or the control 40, which controls an operation of the motor 414. During use, the motor 414 rotates the disk at a prescribed rate such that the first and the second target materials 474, 476 can be alternately placed at a target position. Electrons emitted from the electron gun 402 impinges onto the target materials 474, 476 at the target position, and the interaction of the electrons with the target materials 474, 476 generate x-ray radiation at the first and the second levels, respectively. The speed of rotation of the disk 416 can be modulated such that radiation at the first and second levels can be generated at prescribed times (e.g., in synchronization with image data collection). In some embodiments, the processor 54 controls an operation of the motor 414 such that generation of radiation at the first and second levels are synchronized with prescribed gantry angles. Although four first target materials 474 and four second target materials 476 are shown, in alternative embodiments, the x-ray source assembly 20b can have fewer or more than four sets of the first and the second target materials 474, 476. Also, in alternative embodiments, a region of the disk 416 is not covered by a target material, thereby providing a time gap between successive radiation generation.

FIG. 4C shows another x-ray source assembly 20c in accordance with other embodiments of the invention. The x-ray source assembly 20c is similar to the x-ray source assembly 20a. However, instead of using an electron deflector to modulate a direction of accelerating electrons, the x-ray source assembly 20c includes a positioner 478 coupled to the motor 414. The positioner 478 is configured to move the disk 416 in either of the directions as indicated by arrows 479. The positioner 478 is coupled to the processor 54 and/or the control 40, which controls an operation of the positioner 478. For example, in one embodiment, the processor 54 can gate a transmission of a signal to the positioner 478 such that the positioner 478 can place either the first target material 474 or the second target material 476 at a target position to which the beam 440 of electron is directed. The placement of the first and the second target materials 474, 476 can be performed synchronously with a gantry rotation. To generate radiation at a first energy level, the positioner 478 places the first target material 474 at the target position. The voltage supply 460 then supplies a voltage to the electron gun 402 to generate the electron beam 440. X-rays at a first energy level are generated by the interaction of the electron beam 440 and the first target material 474. To generate radiation at a second energy level, the positioner 478 places the second target material 476 at the target position, and x-rays at the second energy level are generated by the interaction of the electron beam 440 and the second target material 476. In alternative embodiments, instead of positioning the target materials 474, 476, a positioner (not shown) can be coupled to the electron gun 402. In such case, the positioner is configured to position the electron gun 402 such that the electron beam 440 generated therefrom will either impinge the first target material 474 or the second target material 476.

Figure 4D:
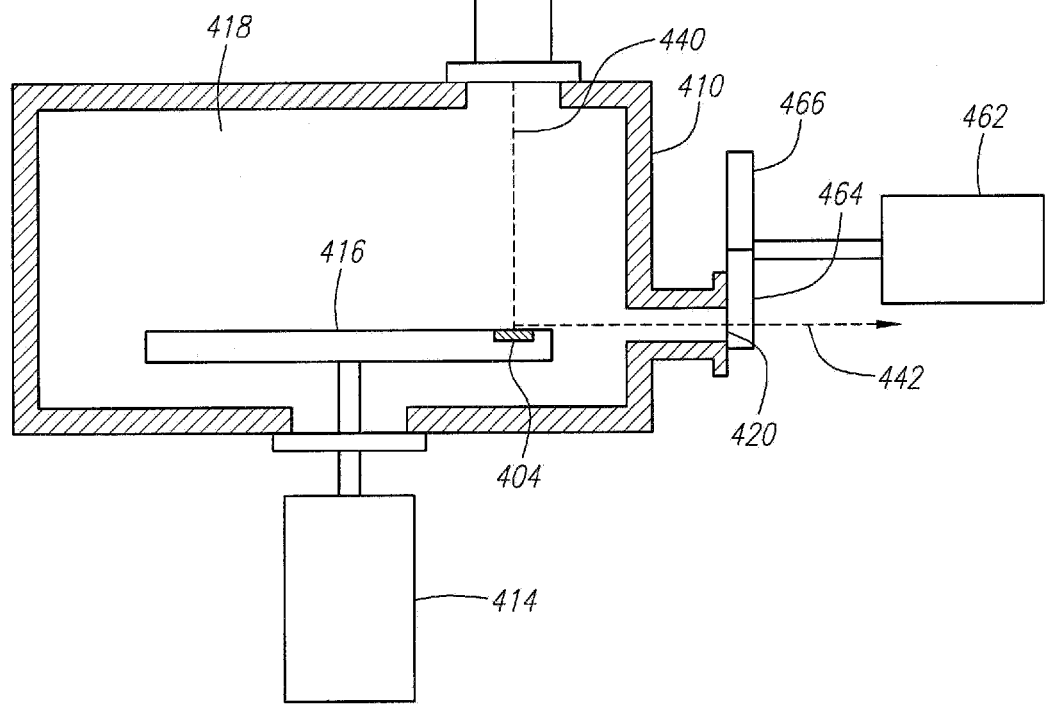

FIG. 4D shows another x-ray source assembly 20d in accordance with other embodiments of the invention. The x-ray source assembly 20d is similar to the x-ray source assembly 20a except that it does not have an electron deflector and that it only has one target material 404. The x-ray source assembly 20d includes a first filter 464 and a second filter 466 secured to a positioner 462. The filters 464, 466 can be made from a variety of materials, such as aluminum, molybdenum, and copper. Also, any of the materials described previously for the target material can also be used. The preferred x-ray filter characteristics are such that the first filter 464 has a high x-ray transmission window in the range corresponding to a transmission window of the contrast material just below the contrast material k-edge, and the second filter 466 has a transmission window about the same width but above the contrast material k-edge. For example, for Gd contrast agent, the filter materials for the first and the second filters 464, 466 may be selected from elements with atomic numbers below 64 (the atomic number of Gd) and above 64, respectively. When determining a preferred filter factors related to a source x-ray spectrum, filteration by tissue, and detector efficiency spectral profile can be considered.

In the illustrated embodiment, the positioner 462 and the voltage supply 460 are coupled to the processor 54 and/or the control 40, which controls an operation of the positioner 462 and the voltage supply 460. For example, in one embodiment, the processor 54 can gate a transmission of a signal to the positioner 462 such that the positioner 462 can place either the first filter 464 or the second filter 466 in front of the x-ray window 420 synchronously with a gantry rotation. To generate radiation having a first characteristic, the positioner 462 places the first filter 464 in front of the x-ray window 420. At least a portion of the x-rays generated from the interaction of the electron beam 440 and the target material 404 exits the x-ray window 420 and impinges on the first filter 464. The impinging x-rays are filtered by the first filter 464 to produce radiation having a first characteristic, e.g., a first energy level.

To generate radiation having a second characteristic, the positioner 462 replaces the first filter 464 in front of the x-ray window 420 with the second filter 466. X-rays exiting the x-ray window 420 impinges on the second filter 464, and are filtered by the second filter 464 to produce radiation having a second characteristic, e.g., a second energy level. Those skilled in the art understand that radiation beam generated using different filter material and/or filter thickness will have different characteristics. As such, different materials can be selected for construction of the filters 464, 466, and/or the thickness of the filters 464, 466 can be designed such that x-ray radiation generated by the x-ray source assembly 20c will have certain desired characteristic(s).

Figure 4E:
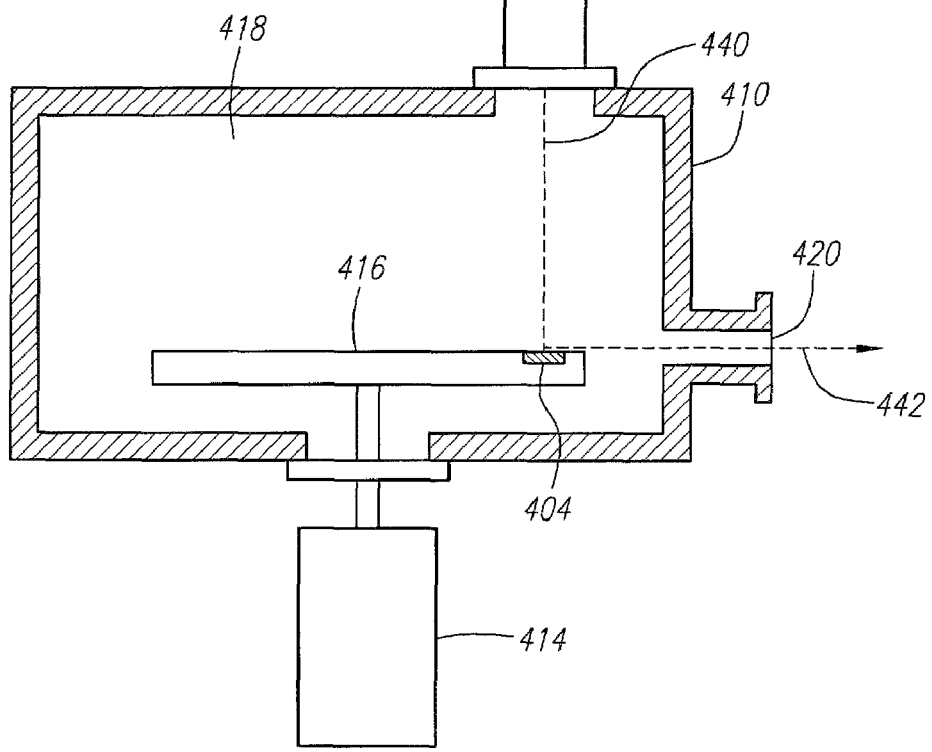

FIG. 4E shows another x-ray source assembly 20e in accordance with other embodiments of the invention. The x-ray source assembly 20e is similar to the x-ray source assembly 20d except that it does not have the filters 464, 466. The x-ray source assembly 20e includes a voltage supply 452 having a switch 454 for switching a supplied voltage between a first level and a second level. To generate radiation at a first energy level, the switch 454 causes the voltage supply 452 to generate a voltage having a first level such that x-ray 442 at the first energy level can be generated. To generate radiation at a second energy level, the switch 454 causes the voltage supply 452 to generate a voltage having a second level such that x-ray 442 at the second energy level can be generated. As similarly discussed previously, the voltage supply 452 can be coupled to the processor 54 and/or the control 40. In some embodiments, the x-ray source assembly 20e can further include one or more filters (similar to the filters 464, 466) for generating radiation having certain desired characteristic(s).

Figure 4F:
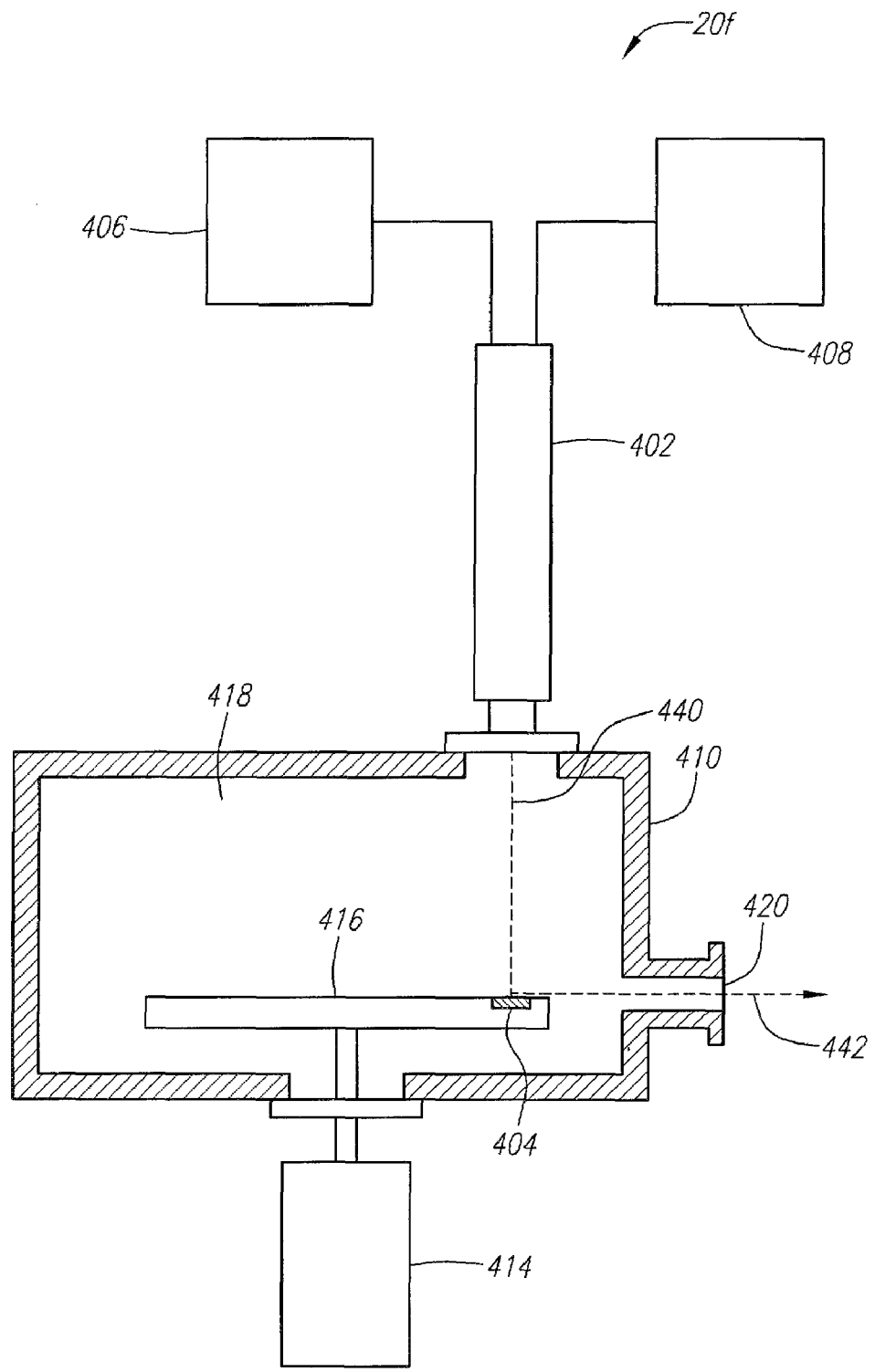

FIG. 4F shows a x-ray source assembly 20f in accordance with other embodiments of the invention. The x-ray source assembly 20f is similar to the x-ray source assembly 20e except that it has two voltage supplies 406, 408 secured to the electron gun 402. The first and the second voltage supplies 406, 408 are configured to supply a first voltage and a second voltage to the electron gun 402, respectively, during use. The voltage supplies 406, 408 are coupled to the processor 54 and/or the control 40, which controls an operation of the voltage supplies 406, 408. For example, the processor 54 can gate a transmission of an activation signal to the voltage supplies 406, 408, such that radiation at the first and second energy levels can be generated at prescribed gantry angles of rotation. During use, the first voltage supply 406 supplies a first voltage to the electron gun 402 to generate a cloud of electrons. Due to a potential that is generated between the electron gun 402 and the target material 404, the electrons accelerate towards the target material 404, forming a beam 440 of electrons. X-rays at a first energy level are generated by the interaction of the electron beam 440 and the target material 404. To generate x-ray beam at a second energy level, the first voltage supply 406 is deactivated and the second voltage supply 408 is activated to supply a second voltage to the electron gun 402. In one embodiment, the first voltage supply 406 supplies a first voltage for generating radiation having an energy level that is below a k-edge of a contrast agent, and the second voltage supply 408 supplies a second voltage for generating radiation having an energy level that is higher than a k-edge of the contrast agent. For example, the first and the second voltages can be selected such that the first and the second x-ray range is between 25% to 50% below and above, respectively, a k-edge of the contrast agent.

It should be noted that although several examples of the x-ray source assembly 20 have been described, the scope of the invention should not be so limited. In alternative embodiments, the x-ray source assembly 20 can have other configurations as long as the x-ray source assembly 20 can deliver radiation at a plurality of energy levels. In addition, in alternative embodiments, a feature described in reference to an embodiment of the x-ray source assembly 20 can be combined with other embodiment(s) of the x-ray source assembly 20. For example, in an alternative embodiment, the x-ray source assembly 20 can include two voltage supplies and two filters. In another embodiment, the x-ray source assembly 20 can have two target materials and two voltage supplies or two filters. Furthermore, in alternative embodiments, the x-ray source assembly 20 can be configured to generate radiation at more than two energy levels. For examples, the x-ray source assembly 20 can include more than two target materials, more than two filters, and/or more than two voltage supplies. Other x-ray source assembly capable of generating radiation at different energy level can also be used. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT", filed on Nov. 2, 2001, the entirety of which is expressly incorporated herein by reference.

Detector Assembly

Figure 5:
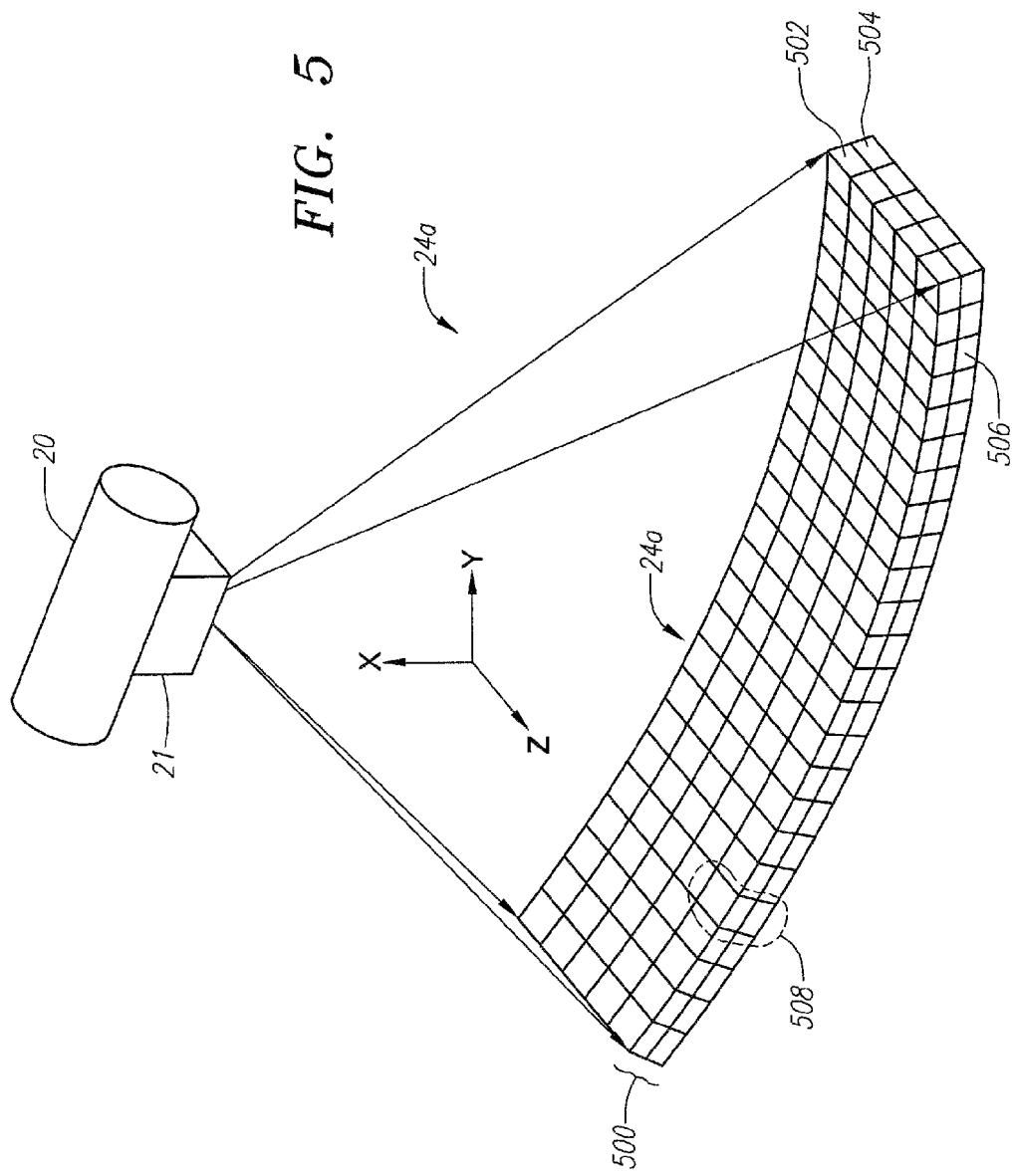
FIG. 5 illustrates a detector assembly in accordance with an embodiment of the invention.

As discussed previously, the detector assembly 24 generates image signal/data in response to radiation impinges thereon. The detector assembly 24 can be variously constructed. FIG. 5 shows a detector assembly 24a in accordance with some embodiments of the invention. The detector assembly 24a comprises an imager 500 that includes a x-ray conversion layer 502 made from a scintillator element, such as Cesium Iodide (CsI), and a photo detector array 504 (e.g., a photodiode layer) coupled to the x-ray conversion layer 502. The x-ray conversion layer 502 generates light photons in response to x-ray radiation, and the photo detector array 504, which includes a plurality of detector elements 506, is configured to generate electrical signal in response to the light photons from the x-ray conversion layer 502. In the illustrated embodiment, both the x-ray conversion layer 502 and the photo detector array 504 are pixilated, thereby forming a plurality of imaging elements 508. However, the x-ray conversion layer 502 may be non-pixilated in an alternative embodiment. In the illustrated embodiment, the imager 500 has a curvilinear surface (e.g., a partial circular arc). Such configuration is beneficial in that each of the imaging elements 508 of the imager 500 is located substantially the same distance from the x-ray source 20 assembly. In alternative embodiments, the imager 500 can have a rectilinear surface or a surface having other profiles. In the illustrated embodiment, each image element 508 (or pixel) has a cross sectional dimension that is approximately 200 microns or more, and more preferably, approximately 400 microns or more. However, image elements having other dimensions may also be used. Preferred pixel size can be determined by a prescribed spatial resolution. The image elements 508 having 200 to 400 microns in cross sectional dimension are good for general anatomy imaging. For breast imaging, image elements 508 having cross sectional dimension that is between 50 to 100 microns are preferred. The imager 500 can be made from amorphous silicon, crystal and silicon wafers, crystal and silicon substrate, or flexible substrate (e.g., plastic), and may be constructed using flat panel technologies (e.g., active-matrix flat panel technologies) or other techniques known in the art of making imaging device.

In one embodiment, each of the image elements 508 comprises a photodiode (forming part of the detector element 506) that generates an electrical signal in response to a light input. The photodiode receives light input from the x-ray conversion layer 502 that generates light in response to x-rays. The photodiodes are connected to an array bias voltage to supply a reverse bias voltage for the image elements. A transistor (such as a thin-film N-type FET) functions as a switching element for the image element 508. When it is desired to capture image data from the image elements 508, control signals are sent to a gate driver to "select" the gate(s) of transistors. Electrical signals from the photodiodes "selected" by the gate driver are then sent to charge amplifiers, which outputs image signals/data for further image processing/display.

In one embodiment, the image data are sampled from the image elements 508 one line at a time. Alternatively, the image data from a plurality of lines of the image elements 508 can be sampled simultaneously. Such arrangement reduces the time it takes to readout signals from all lines of image elements 508 in the imager 500. This in turn, improves a frame rate (i.e., number of frames that can be generated by the imager 500 per second) of the imager 500. Devices and methods for simultaneously collecting image data from a plurality of lines of image elements have been described in U.S. patent application Ser. No. 10/687,552, entitled "Multi-slice flat panel computed tomography", filed concurrently herewith, the entire disclosure of which is expressly incorporated by reference herein.

During use, radiation at a first energy level impinges on the detector assembly 24a, which then generates image signals/data in response to the radiation at the first energy level. After the image signals/data are read out from the photo detector array 504, radiation at a second energy level is directed to the detector assembly 24a. The assembly 24a then generates image signals/data in response to the radiation at the second energy level. In one embodiment, one or more filters can be placed between the x-ray source assembly 20 and the detector assembly 24 (e.g., on top of the conversion layer 502) before radiation at either or both of the energy levels is directed to the detector assembly 24a. The filter(s) alters radiation exiting from the patient 16, such that radiation having a desired characteristic will be received by the detector assembly 24a. In one embodiment, a first filter(s) can be used to maximize or optimize a detective quantum efficiency of the detector assembly 24a for radiation at a first energy level, while a second filter(s) can be used to maximize or optimize detective quantum efficiency of the detector assembly 24a for radiation at a second energy level. For example, the detector assembly 24a may have a uniform sensitivity to all photon energies in a spectrum, may have a sensitivity that is proportional to photon energy, or may have "holes" where photons of certain energy ranges are not efficiently absorbed. For each of these different types of detector assembly 24a, one or more filters can be selected to maximize an efficiency of the system 10 (e.g., maximizing a response of the system 10 in measuring the injected contrast agent, and/or minimizing dose delivery and time). The placement of the filter(s) can be accomplished manually or mechanically. In some embodiments, the filters can be parts of the detector assembly 24.

Figure 6:
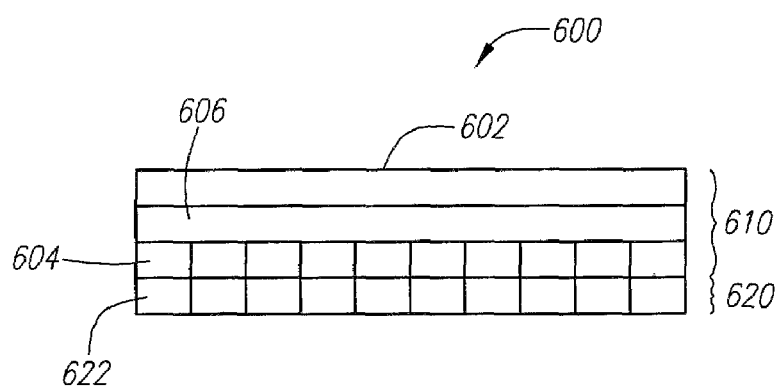
FIG. 6 illustrates a variation of the detector assembly of FIG. 5, showing the detector assembly having a photoconductor.

In alternative embodiments, the detector assembly 24 may use different detection schemes. For example, in alternative embodiments, instead of having the x-ray conversion layer 502, the detector assembly 24 can include an imager having a photoconductor, which generates electron-hole-pairs or charges in response to x-ray. FIG. 6 schematically shows an imager 600 constructed in accordance with alternative embodiments of the present invention. The imager 600, which can be a flat panel imager, for example, includes a x-ray conversion panel 610 aligned with a detector array 620. The x-ray conversion panel 610 includes a first electrode 602, a second electrode 604, and a photoconductor 606 secured between the first electrode 602 and the second electrode 604. The electrodes 602, 604 can be made from a wide variety of materials, such as silver, chromium, aluminum, gold, nickel, vanadium, zinc, palladium, platinum, carbon, etc., and alloys of these materials. The photoconductor 506 can be made from a variety of photo conductive materials, such as mercuric Iodide ($HgI_2$), Lead Iodide ($PbI_2$), Bismuth Iodide ($BiI_3$), Cadmium Zinc Telluride (CdZnTe), Amorphous Selenium (a-Se), or equivalent thereof. $HgI_2$ and $PbI_2$ are particularly preferred because these materials efficiently absorb x-ray photons and have desirable photo conductive properties. Photoconductor screens (or panels) from these materials can increase a modulation transformer function (MTF) value—a measure of spatial resolution, thereby providing high radiograph quality. Other materials known in the art may also be used. The photoconductor 606 may be a single or poly-crystalline layer, or an amorphous layer. The photoconductor 606 is preferably deposited by physical vapor depositon (PVD) or particle in binder process (PIB). Alternatively, the photoconductor 606 may also be secured to the first and second electrodes 602 and 604 by a suitable adhesive, depending on the materials from which the photoconductor 606 and the first and second electrodes 602 and 604 are made. Other techniques known in the art may also be used to secure the photoconductor 606 to the first and second electrodes 602 and 604. Photoconductors and imagers made therefrom are well known in the art, and therefore would not be described in further details herein.

When using the imager 600, the first and second electrodes 602 and 604 are biased by a voltage source to create a potential difference or a bias between the first and second electrodes 602 and 604. The biased electrodes 602 and 604 create an electric field across the region between the first and second electrodes 602 and 604. When the photoconductor 606 is irradiated by x-ray, a response, such as electron hole pairs (EHPs) or charges, are generated and drift apart under the influence of the electric field across the region between the first and second electrodes 602 and 604. The charges are collected by the detector array 620, which includes a plurality of detector elements 622 arranged in a two-dimensional array. The detector elements 622 are configured to generate electric signals in response to the charges collected on the first electrode 602. In one embodiment, the detector elements 622 are amorphous silicon (a-Si:H) charge detectors. Each detector element 622 may have a storage capacitor to store the charge generated by the X-rays and collected by the first electrode 602. Each detector element 622 may also include a switching element, such as a thin film transistor (TFT), a switching diode, or the like, to access the collected charge by readout electoronics. Optionally the detector elements 622 can contain further components for signal or charge buffering and amplification. The detector elements 622 can also include polycrystalline silicon or organic active elements. Each of the detector elements 622 forms a pixel of the X-ray image generated using the detector array 620. The detector array 620 also includes a pixel access circuit (not shown) coupled to detector elements 622. The pixel access circuit accesses the detector elements 622 and reads the electric signals from the detectors elements 622. In one embodiment, pixel access circuit includes a gate driver that generates row access signals to sequentially access detector elements 622 by rows and reads electric signals out of detector elements 622 by columns. Each row access signal can access either a single row or multiple rows of detectors elements 622. Likewise, each read action can read electric signals from either a single column or a plurality of columns of the detectors elements 622. The process of accessing detector elements 622 and reading electric signals there from is well known in the art, and therefore, would not be describe in further detail. In some embodiments, one or more filters can be placed between the x-ray source assembly 20 and the detector assembly 24 (e.g., on top of the electrode 602 or on top of the photoconductor 606) before radiation at either or both of the energy levels is directed to the detector assembly 24, as similarly discussed previously.

Other detection schemes can also be used. In alternative embodiments, the detector assembly 24 can be configured to detect photon pulse amplitude and/or photon count. Such arrangement allows a pulse amplitude spectrum of one or more x-ray photon events to be measured on a pixel by pixel basis. In such case, the pulse amplitudes can be processed to create desired image data. For example, in one embodiment, image data can be created by considering pulse amplitudes that are above a prescribed threshold. Detectors capable of detecting photon pulse amplitudes and photon count have been described in U.S. patent application Ser. No. 10/438,684, the entire disclosure of which is expressly incorporated by reference herein.

Figure 7:
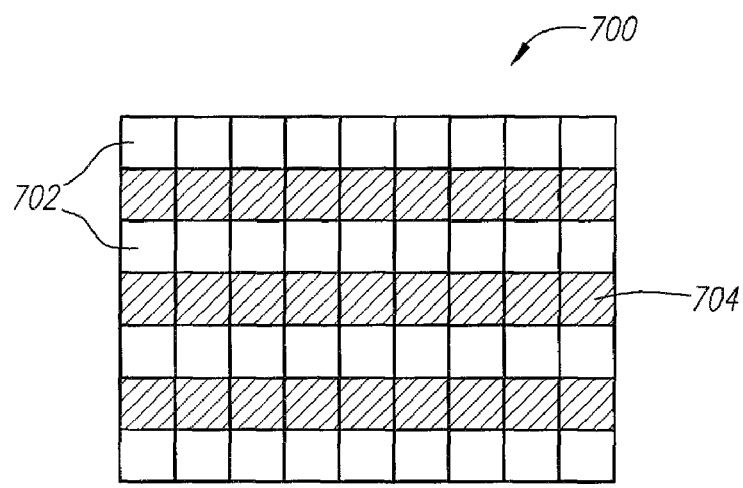
FIG. 7 illustrates an imager in accordance with another embodiment of the invention.

FIG. 7 shows another imager 700 in accordance with other embodiments of the invention. The imager 700 includes a plurality of first imaging elements 702 and second imaging elements 704. Each of the first and the second imaging elements 702, 704 is similar to the imaging element 508 described previously.

In the illustrated embodiments, each of the first imaging elements 702 includes a first conversion element (or a scintillating material) having a first radiation conversion characteristic, and each of the second imaging elements 704 includes a second conversion element having a second radiation conversion characteristic. By means of non-limiting examples, a radiation conversion characteristic can be a sensitivity of reaction to radiation, a quantity of photons created per unit of radiation, a photon generation efficiency, and other variables related to any of these characteristics. For example, the first conversion element can be made from one of the materials selected from the group that includes mercuric Iodide ($HgI_2$), Lead Iodide ($PbI_2$), Bismuth Iodide ($BiI_3$), Cadmium Zinc Telluride (CdZnTe), and Amorphous Selenium (a-Se), while the second conversion element can be made from another material selected from the group. Each of these materials has a different k-edge, and the screen thickness can be chosen to generate a detector with "holes" (low efficiency bands) and "sinks" (high efficiency bands) that are below and above the k-edge(s), respectively. In some embodiments, either or both of the first and the second conversion elements can be made from more than one materials. This allows multiple "holes" and "sinks" at various k-edge related photon energies be generated. The first and the second conversion elements together form a conversion panel. The imager 700 also includes a photo detector array aligned with the conversion panel. The photo detector array comprises a plurality of detector elements configured to generate a signal in response to light photons received from the conversion panel. An access circuit (not shown) is coupled to the photo detector array and is configured to collect signals from one or more lines of the detector elements in the photo detector array. In some embodiments, all of the detector elements has similar functional characteristics. In other embodiments, the photo detector array can include a plurality of first detector elements configured to generate signals in response to photons having a first energy level, and a plurality of second detector elements configured to generate signals in response to photons having a second energy level.

In alternative embodiments, each of the first and the second imaging elements 702, 704 includes a photoconductor layer, as similarly discussed previously. In such case, each of the first imaging elements 702 includes a first photoconductor element (e.g., a layer) having a first charge generation characteristic, and each of the second imaging elements 704 includes a second photoconductor element having a second charge generation characteristic. By means of non-limiting examples, a charge generation characteristic can be a sensitivity of reaction to radiation, a quantum level of charges created per unit of radiation, a charge generation efficiency, and other variables related to any of these characteristics. Any of the materials discussed previously with reference to FIG. 6 can be used to construct the first and the second photoconductor elements. For example, the first photoconductor element can be made from one material, and the second photoconductor element can be made from another material. Alternatively, or additionally, the first and the second photoconductor elements can also have different thicknesses. The first and the second photoconductor elements together form a photoconductor layer. The imager 700 also includes a photo detector array aligned with the photoconductor layer. The photo detector array comprises a plurality of detector elements configured to generate a signal in response to charges received from the photoconductor layer. An access circuit (not shown) is coupled to the photo detector array and is configured to collect signals from one or more lines of the detector elements in the photo detector array. In some embodiments, all of the detector elements has similar functional characteristics. In other embodiments, the photo detector array can include a plurality of first detector elements configured to generate signals in response to charges having a first quantum level, and a plurality of second detector elements configured to generate signals in response to charges having a second quantum level.

In the illustrated embodiment, the first and the second image elements 702, 704 are arranged in rows (or columns), such that a row of the first image elements 702 are located adjacent a row of the second image elements 704. In alternative embodiments, instead of having the alternate row arrangement, the first and the second image elements 702, 704 can be positioned relative to each other in other arrangements. For example, the first and the second image elements 702, 704 can be arranged relative to each other in a checkerboard pattern.

In some embodiments, the first and the second image elements 702, 704 are used to generate image signal/data in response to radiation at a first energy level and a second energy level, respectively. Missing data between rows of the first image elements 702, and missing data between rows of the second image elements 704 can be generated by interpolation. In other embodiments, the first image elements 702 only generate image signal/data in response to radiation at a second energy level, and are deactivated when radiation at a first energy level is being applied. The second image elements 704 are activated when radiation at the first and second energy levels are being applied. In such case, missing data between rows of the first image elements 702 can be interpolated to obtain a first set of image data for a first image that corresponds to radiation at the second energy level. To obtain a second image that corresponds to radiation at the first energy level, missing data between rows of the second image elements 704 can be interpolated to obtain a second set of image data, and the first set of image data is then subtracted from the second set of image data to generate the second image. Other similar techniques or algorithms can also be used.

It should be noted that the configuration of the x-ray imager 24 should not be limited to the examples discussed previously. By way of example, U.S. patent application Ser. No. 10/439,350, entitled "MULTI ENERGY X-RAY IMAGER" filed on May 15, 2003, discloses x-ray imaging devices capable of generating signals in response to multiple radiation energy levels, and can be used as the detector assembly 24. U.S. patent application Ser. No. 10/439,350 is incorporated herein by reference in its entirety. In addition, U.S. patent application Ser. No. 10/013,199 entitled "X-RAY IMAGE ACQUISITION APPARATUS" and filed on Nov. 2, 2001 discloses an X-ray image detecting device that is capable of detecting multiple energy level X-ray images, and can also be used as the detector assembly 24 in accordance with the present invention. U.S. patent application Ser. No. 10/013,199 is incorporated herein by reference in its entirety.

Figure 8:
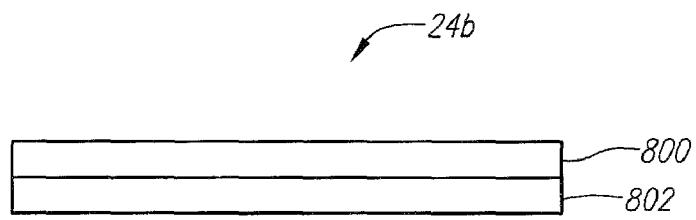
FIG. 8 illustrates a detector assembly having a plurality of imagers in accordance with another embodiment of the invention.

In the above described embodiments, the detector assembly 24 includes a single imager for generating image data. However, in alternative embodiments, the detector assembly 24 can include a plurality of imagers, with each configured to generate image data in response to a prescribed range of radiation levels. FIG. 8 shows a detector assembly 24b that includes a plurality of imagers, in accordance with some embodiments of the invention. The detector assembly 24b includes a first detector 800, and a second detector 802 located behind the first detector 800. The first detector 800 is configured to generate image signal/data in response to radiation at a first level, and the second detector 800 is configured to generate image signal/data in response to radiation at a second level. Either or both of the detectors 800, 802 can include a layer of scintillating material or a photoconductor, as similarly discussed previously. During use, radiation at a first energy level impinges on the first detector 800 and the first detector 800 generates a first set of image signal/data in response to the radiation. After the image signal/data are read from the first detector 800, radiation at a second energy level is directed to the detector assembly 24b. In some embodiments, radiation at the second energy level is not substantially attenuated by the first detector 800, thereby allowing the second detector 802 to generate image signal/data in response to radiation that passes through the first detector 800. Alternatively, the first detector 800 can be constructed such that radiation can pass between image elements of the first detector 800. For example, each of the image elements of the first detector 800 can be separated from an adjacent image element such that a gap is provided to allow radiation to pass to the second detector 802. In such case, the first detector 800 generates image signal/data in response to radiation at a first energy level impinging thereon, and the second detector 802 generates image signal/data in response to radiation at a second energy level that has passed between the image elements of the first detector 800.

Computed tomography (CT) and Cone Beam CT Reconstruction

CT or CBCT defines a volume, $VOI_{point}$, around an image point and measures the average x-ray attenuation of the material in this volume relative to that of water. In rectilinear (parallel beam) geometry this volume is independent of location of the point in the image. The achievement of good reconstructed image quality for other geometries depends on the success of the reconstruction algorithm's ability to achieve this independence for other data collection geometries.

Denoting $S_{Obj}(E_{eff}, r)$ as the average object attenuation at a point in an object being imaged, and averaging over the reconstruction point volume VOI$_{point}$ where $s_{Obj}(E, r)$ is the objects attenuation cross-section, and $r_{Obj}(r)$ is the objects density at position r, yields:

$$\Sigma_{Obj}(E_{\mathit{eff}\_v}, r) \equiv \frac{\int_0^{Vol_{point}} \sigma_{Obj}(E, r) \cdot \rho_{Obj} dr}{\int_0^{Vol_{point}} 1 dr}$$

where it is assumed that the photon energy spectrum is considered a delta function and that the $E_{\mathit{eff}\_v}$ is chosen appropriately. For a uniform material such as water this becomes: $\Sigma_{H2O}(E_{\mathit{eff}\_v}, r) \equiv \sigma_{H2O}(E) \cdot \rho_{H2O}$. Hence, if a point in the object has an attenuation HU$_{Object}$, the Vol$_{point}$ averaged attenuation at that point, $S_{Obj}(E_{\mathit{eff}\_v})$, is:

$$\Sigma_{Obj}(E_{\mathit{eff}\_v}) \equiv \frac{(HU_{Object} + 1000)}{1000} \cdot (\sigma_{H2O}(E_{\mathit{eff}\_v}) \cdot \rho_{H2O})$$

An A-to-D counts (ADCounts) as measured by a detector, for the case when no object is placed between a radiation source and the detector assembly can be expressed in the following equation:

ADCountsThru$_{Air}$·ΔA≡(S_Fact·∫φ(E)·ψdet(E)dE)·ΔA
where φ (E)

represents a flux (x-ray photons incident per unit area) created by a radiation source, as determined by source characteristics, and ψdet(E) represents a detector efficiency. ΔA should be less than or equal to the nominal area cross section of the reconstruction volume. An ADCounts for the case when an object is placed between the radiation source and the detector assembly can be expressed by the following equation:

ADCountsThru$_{Obj}$(L)·Δ

$$A \equiv \left[S\_Fact \cdot \int \phi(E) \cdot \psi det(E) \cdot e^{-\left(\sum_{L=0}^{ThruObject} \Sigma_{Obj}(E_{\mathit{eff}\_v}, r) \Delta L\right)} dE \right] \cdot \Delta A$$

where S_Fact is a scaling factor that represents voltage per photon, and $E_{\mathit{eff}\_v}$ represents effective energy that has taken into consideration a change of sigma ($\Sigma_{Obj}$).

In the above equation, a change in φ (E) along a path is neglected. A change in φ (E) with position has an affect on $S_{Obj}(E_{\mathit{eff}}, r)$. The reconstruction algorithm itself assumes that the $S_{Obj}(E_{\mathit{eff}}, r)$ is independent of the direction of the beam defining the L direction and also the direction of the incident beam passing along. Generally, as a first approximation, the above considerations are neglected, and it is assumed that the photon energy spectrum is considered a delta function and that the $E_{\mathit{eff}\_s}$ is chosen appropriately to consider a change of spectrum of the flux along a path. Appropriate $E_{\mathit{eff}\_v}$ and $E_{\mathit{eff}\_s}$ are not necessarily equal. Then the above gives the transmission as follows:

$$TransmissionAlong(L, E_{\mathit{eff}\_s}) \equiv \frac{ADCountsThru_{Obj}(L) \cdot \Delta A}{ADCountsThru_{Air} \cdot \Delta A} \text{ or}$$

-continued $$\left[\sum_{L=0}^{ThruObject} (\Sigma_{Obj}(E_{\mathit{eff}\_sv}, r) \cdot \Delta L\right] \equiv -\ln\left(\frac{ADCountsThru_{Obj}(L)}{ADCountsThru_{Air}}\right),$$

where $E_{\mathit{eff}\_sv}$ represents effective energy that has taken into consideration the change of sigma and a change of a spectrum of the flux along a path. CBCT uses these line integrals to reconstruct the value of $\Sigma_{Obj}(E_{\mathit{eff}\_v}, r)$ throughout the object volume. The effect of the various approximations discussed above can be reduced by reconstructing the difference image between a uniform "norm" object constructed from material e.g. H$_2$O which results in similar observed line integrals. Then, ADCountsThru$_{H2O}$(L)·Δ

$$A \equiv \left[S\_Fact \cdot \int \Phi(E) \cdot \psi det(E) \cdot e^{-\left(\sum_{L=0}^{ThruH2O} \Sigma_{H2O}(E_{\mathit{eff}\_v}, r) \Delta L\right)} dE\right] \cdot \Delta A$$

and $$\left[\sum_{L=0}^{ThruObject} (\Sigma_{Obj}(E_{\mathit{eff}\_sv}, r) - \Sigma_{H2O}(E_{\mathit{eff}\_sv}, r)) \cdot \Delta L\right] \equiv$$

$$-\ln\left(\frac{ADCountsThru_{Obj}(L)}{ADCountsThru_{H2O}}\right).$$

The quantity $\Sigma_{Obj}(E_{\mathit{eff}\_sv}, r) - \Sigma_{H2O}(E_{\mathit{eff}\_sv}, r)$ can then be reconstructed.

Similarly, when using a filter in the incident beam, a change in the beam energy spectrum can be represented as follows:

$$\left[\sum_{L=0}^{ThruObject} (\Sigma_{Obj}(E_{\mathit{eff}\_sov}, r) - \Sigma_{Obj}(E_{\mathit{eff}\_sfv}, r)) \cdot \Delta L\right] \equiv$$

$$-\ln\left(\frac{ADCountsSpectNoFilter_{Obj}(L)}{ADCountsSpectFilter_{Obj}(L)}\right)$$

where $E_{\mathit{eff}\_sov}$ represents effective energy when no filter is used, and $E_{\mathit{eff}\_sfv}$ represents effective energy when a filter is used. In such case, the quantity $E_{Obj}(E_{\mathit{eff}\_sov}, r) - \Sigma_{H2O}(E_{\mathit{eff}\_sfv}, r)$ can be reconstructed. Those skilled in the art understand that similar techniques can be used for the cases when different contrast agents, different voltages and/or different target materials are used to create radiation at multiple energy levels. Other reconstruction algorithms known in the art can also be used. Cone beam CT has been described in U.S. patent application Ser. No. 10/324,227, entitled, "A multi-mode cone beam CT radiotherapy simulator and treatment machine with a flat panel imager", filed Dec. 17, 2002, the entire disclosure is expressly incorporated by reference herein.

Computer System Architecture

Figure 9:
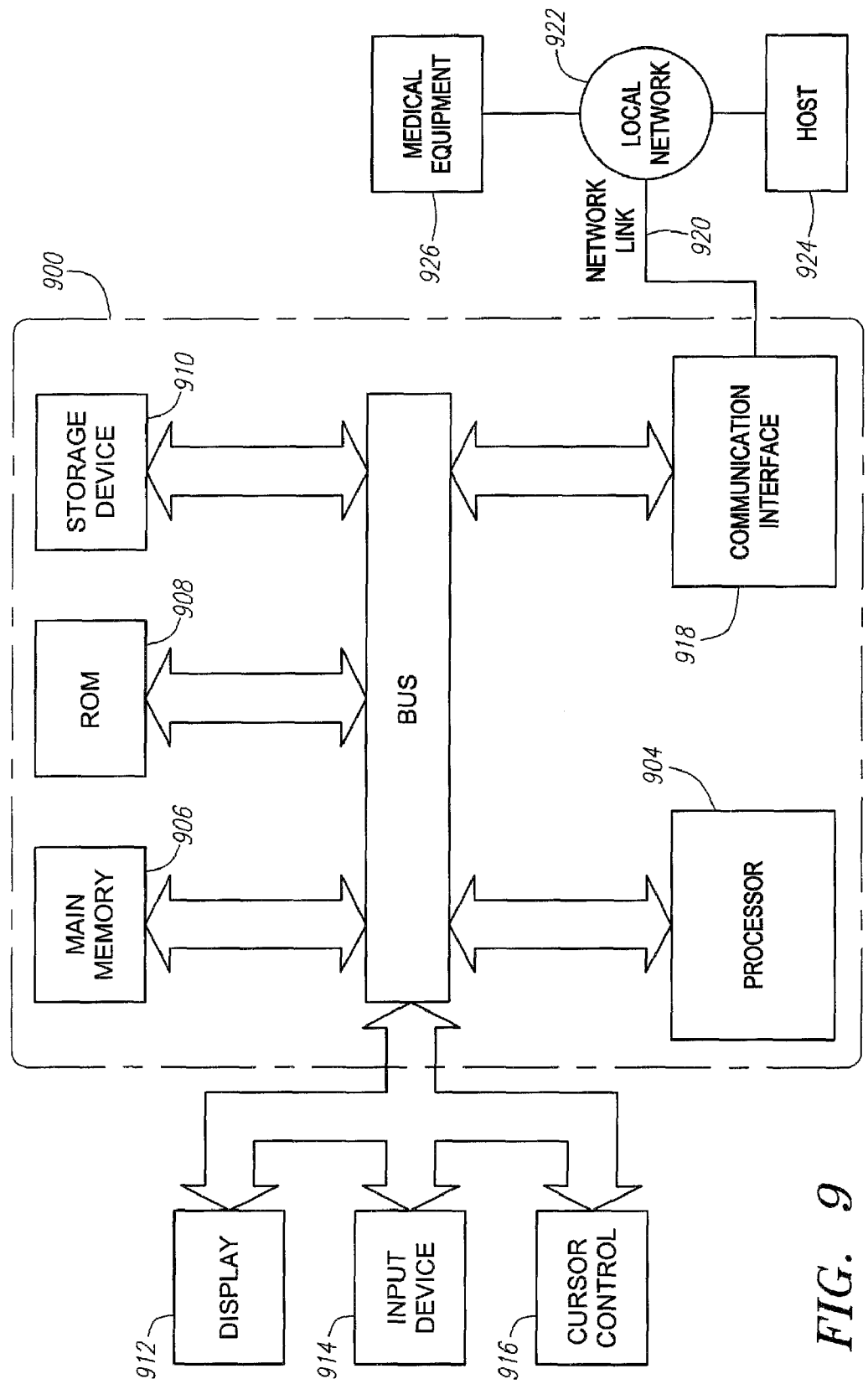
FIG. 9 is a diagram of a computer hardware system with which embodiments of the present invention can be implemented.

FIG. 9 is a block diagram that illustrates an embodiment of a computer system 900 upon which an embodiment of the invention may be implemented. Computer system 900 includes a bus 902 or other communication mechanism for communicating information, and a processor 904 coupled with the bus 902 for processing information. The processor 904 may be an example of the processor 54, or alternatively, an example of a component of the processor 54, of FIG. 1. The computer system 900 also includes a main memory 906, such as a random access memory (RAM) or other dynamic storage device, coupled to the bus 902 for storing information and instructions to be executed by the processor 904. The main memory 906 also may be used for storing temporary variables or other intermediate information during execution of instructions to be executed by the processor 904. The computer system 900 further includes a read only memory (ROM) 908 or other static storage device coupled to the bus 902 for storing static information and instructions for the processor 904. A data storage device 910, such as a magnetic disk or optical disk, is provided and coupled to the bus 902 for storing information and instructions.

The computer system 900 may be coupled via the bus 902 to a display 912, such as a cathode ray tube (CRT), for displaying information to a user. An input device 914, including alphanumeric and other keys, is coupled to the bus 902 for communicating information and command selections to processor 904. Another type of user input device is cursor control 916, such as a mouse, a trackball, or cursor direction keys for communicating direction information and command selections to processor 904 and for controlling cursor movement on display 912. This input device typically has two degrees of freedom in two axes, a first axis (e.g., x) and a second axis (e.g., y), that allows the device to specify positions in a plane.

The invention is related to the use of computer system 900 for collecting and processing image data. According to one embodiment of the invention, such use is provided by computer system 900 in response to processor 904 executing one or more sequences of one or more instructions contained in the main memory 906. Such instructions may be read into the main memory 906 from another computer-readable medium, such as storage device 910. Execution of the sequences of instructions contained in the main memory 906 causes the processor 904 to perform the process steps described herein. One or more processors in a multi-processing arrangement may also be employed to execute the sequences of instructions contained in the main memory 906. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 904 for execution. Such a medium may take many forms, including but not limited to, non-volatile media, volatile media, and transmission media. Non-volatile media includes, for example, optical or magnetic disks, such as the storage device 910. Volatile media includes dynamic memory, such as the main memory 906. Transmission media includes coaxial cables, copper wire and fiber optics, including the wires that comprise the bus 902. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 904 for execution. For example, the instructions may initially be carried on a magnetic disk of a remote computer. The remote computer can load the instructions into its dynamic memory and send the instructions over a telephone line using a modem. A modem local to the computer system 900 can receive the data on the telephone line and use an infrared transmitter to convert the data to an infrared signal. An infrared detector coupled to the bus 902 can receive the data carried in the infrared signal and place the data on the bus 902. The bus 902 carries the data to the main memory 906, from which the processor 904 retrieves and executes the instructions. The instructions received by the main memory 906 may optionally be stored on the storage device 910 either before or after execution by the processor 904.

The computer system 900 also includes a communication interface 918 coupled to the bus 902. The communication interface 918 provides a two-way data communication coupling to a network link 920 that is connected to a local network 922. For example, the communication interface 918 may be an integrated services digital network (ISDN) card or a modem to provide a data communication connection to a corresponding type of telephone line. As another example, the communication interface 918 may be a local area network (LAN) card to provide a data communication connection to a compatible LAN. Wireless links may also be implemented. In any such implementation, the communication interface 918 sends and receives electrical, electromagnetic or optical signals that carry data streams representing various types of information.

The network link 920 typically provides data communication through one or more networks to other devices. For example, the network link 920 may provide a connection through local network 922 to a host computer 924 or to a medical equipment 926. The data streams transported over the network link 920 can comprise electrical, electromagnetic or optical signals. The signals through the various networks and the signals on the network link 920 and through the communication interface 918, which carry data to and from the computer system 900, are exemplary forms of carrier waves transporting the information. The computer system 900 can send messages and receive data, including program code, through the network(s), the network link 920, and the communication interface 918.

Although the above embodiments have been described with reference to dual-energy, contrast-enhanced cone beam CT imaging of breasts, the scope of the invention should not be so limited. In alternative embodiments, any of the above described devices or methods (or similar devices or methods) can be used to perform imaging of other portions of a body, such as a liver, a chest, a heart, or other vascular structures. In addition, besides using the above techniques for detecting cancerous breast tissue, any of the devices and/or methods described herein can also be used to detect other cancerous tissue or other types of tissue. For example, a contrast agent and/or energy levels of radiation can be selected such that feature(s) of tissue having certain characteristics can be enhanced using any of the above described techniques.

Also, in alternative embodiments, instead of generating a composite image for static visualization, a plurality of composite images can be created for different phases (or phase intervals) of a physiological cycle, and the created composite images can be displayed in a sequence to form a video. For example, a patient positioning monitoring system can be used to collect motion data representative of a motion of the patient 16, while the gantry 12 rotates about the patient 16 (or object being imaged) to generate image data using radiation at a first and second energy levels. The motion data and the image data can be retrospectively synchronized to a common time base, thereby allowing composite images that correspond to different times of the physiological cycle to be created. In one embodiment, the image data can be time-binned based on prescribed phase ranges of a physiological cycle. In an alternative embodiment, the image data can be time-binned based on prescribed amplitude ranges of the physiological cycle. Systems and methods for monitoring patient's position, time-binning based on phase or amplitude ranges, and retrospective gating have been describe in U.S. patent application Ser. No. 10/678,741, entitled, "Method and system for radiation application", filed on Oct. 3, 2003, the entire disclosure of which is herein incorporated by reference.

In addition, instead of using cone beam CT, other imaging techniques, such as Spiral CT, Fan Beam CT, laminar tomography, MRI, or PET, can be used in a similar process to obtain a composite image from a first image and a second image. For example, for MRI, a contrast agent that affects an environment of protons can be selected.

Furthermore, besides using the system 10 to obtain dual-energy contrast-enhanced images, any of the embodiments of the system 10, or components of the system 10, can be used for other applications. For example, in some embodiments, the x-ray source assembly 20 can deliver radiation at a first level for imaging a target object, and radiation at a second level for treating the target object.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. For example, the operations performed by the processor 54 can be performed by any combination of hardware and software within the scope of the invention, and should not be limited to particular embodiments comprising a particular definition of "processor". In addition, the term "image" as used in this specification includes image data that may be stored in a circuitry or a computer-readable medium, and should not be limited to image data that is displayed visually. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed is:

1. A method of generating one or more images of a portion of a body, comprising:
   introducing a contrast agent into the body;
   generating a first set of image data using radiation at a first energy level after the contrast agent is introduced into the body;
   generating a second set of image data using radiation at a second energy level after the contrast agent is introduced into the body;
   creating a contrast-enhanced volumetric composite image using the first and the second sets of image data, wherein the contrast-enhanced volumetric composite image is created such that at least a portion of the contrast-enhanced volumetric composite image has a feature indicating cancerous tissue, and that an image contrast for bone and tissue that does not contain the contrast agent at another portion of the contrast-enhanced volumetric composite image is reduced;
   at least one of storing the contrast-enhanced volumetric composite image and displaying the contrast-enhanced volumetric composite image;
   determining information regarding time-resolved kinetics of the contrast agent in the body based at least in part on the volumetric composite image;
   providing a first graphic that indicates the determined information; and
   providing a second graphic that indicates time-resolved kinetics of a contrast agent in normal tissue, the contrast agent in the normal tissue being a same type as the contrast agent in the body;
   wherein the first and second graphics are provided in a same graph for comparison.

2. The method of claim 1, wherein the contrast agent includes an element selected from the group consisting of iodine, gadolinium, holmium, erbium, lanthanum, cerium, praseodymium, neodymium, samarium, europium, terbium, dysprosium, thulium, ytterbium, and lutetium.

3. The method of claim 1, wherein the portion of the body comprises at least a portion of a breast.

4. The method of claim 1, wherein the first energy level is below a k-edge of the contrast agent.

5. The method of claim 1, wherein the second energy level is above a k-edge of the contrast agent.

6. The method of claim 1, wherein the first and the second sets of image data are generated by performing a computed tomography procedure.

7. The method of claim 6, wherein the computed tomography procedure is performed using a cone beam.

8. The method of claim 1, wherein the first and the second sets of image data are generated by performing a MRI procedure.

9. The method of claim 1, wherein the first and the second sets of image data are generated by performing a PET procedure.

10. The method of claim 1, wherein the volumetric composite image is created by subtracting the first set of image data from the second set of image data.

11. The method of claim 1, wherein the volumetric composite image is created by
   modifying the first set of image data;
   modifying the second set of image data; and
   subtracting the first modified set of image data from the second modified set of image data.

12. The method of claim 11, wherein the acts of modifying comprises applying a logarithmic transform to the first and the second sets of image data.

13. The method of claim 1, wherein the first and the second sets of image data are generated within 5 to 20 microseconds.

14. The method of claim 1, wherein the radiation at either or both of the first and the second energy levels are generated using a multi-energy x-ray source assembly.

15. The method of claim 1, wherein the volumetric composite image is created by removing a tissue feature, and retaining a feature attributable to the contrast agent.

16. The method of claim 1, wherein the radiation at the first and the second energy levels are generated by switching a x-ray tube voltage between a first and a second levels.

17. The method of claim 1, wherein the radiation at the first and the second energy levels are generated by impinging an electron beam onto a first target material and a second target material, respectively.

18. The method of claim 1, wherein the radiation at the first and the second energy levels are generated by filtering x-rays through a first filter and a second filter, respectively.

19. The method of claim 1, wherein the first set of image data comprises data sufficient for generating a volumetric image.

20. The method of claim 1, wherein the first set of image data comprises a plurality of image frames generated by placing a radiation source in different orientations.

21. The method of claim 20, wherein the radiation source is coupled to a gantry, and the act of placing the radiation source in different orientations comprises placing the radiation source at a first gantry angle, and placing the radiation source at a second gantry angle.

22. The method of claim 1, wherein the volumetric composite image is created by determining a first volumetric image from the first set of image, determining a second volumetric image from the second set of image, and subtracting the first volumetric image from the second volumetric image.

23. The method of claim 1, wherein the volumetric composite image is created by obtaining a set of composite images using the first and second sets of image data, the set of composite images being two-dimensional images, and constructing the volumetric composite image using the set of composite images.

24. A system of generating one or more images of a portion of a body after a contrast agent is introduced into the body, the system comprising:
   means for generating a first set of image data using radiation at a first energy level after the contrast agent is introduced into the body;
   means for generating a second set of image data using radiation at a second energy level after the contrast agent is introduced into the body, wherein the first energy level is below a k-edge of the contrast agent, and the second energy level is above a k-edge of the contrast agent;
   means for creating a contrast-enhanced volumetric composite image using the first and the second sets of image data, wherein the means for creating is configured to create the contrast-enhanced volumetric composite image such that at least a portion of the contrast-enhanced volumetric composite image has a feature indicating cancerous tissue, and that an image contrast for bone and tissue that does not contain the contrast agent at another portion of the contrast-enhanced volumetric composite image is reduced;
   means for determining information regarding time-resolved kinetics of the contrast agent in the body based at least in part on the volumetric composite image; and
   means for displaying a first graphic and a second graphic in a same graph, wherein the first graphic indicates the determined information, and the second graphic indicates time- resolved kinetics of a contrast agent in normal tissue, the contrast agent in the normal tissue being a same type as the contrast agent in the body.

25. The system of claim 24, wherein the means for generating the first and the second sets of image data comprises one or more imagers.

26. The system of claim 24, further comprising a x-ray source assembly for generating the radiation at the first and the second energy levels, the x-ray source assembly having one or more target materials.

27. The system of claim 24, further comprising a x-ray source assembly for generating the radiation at the first and second energy levels, wherein the x-ray source assembly comprises a plurality of filters for filtering x-ray.

28. The system of claim 24, further comprising a x-ray source assembly for generating the radiation at the first and second energy levels, wherein the x-ray source assembly comprises a plurality of the target materials.

29. The system of claim 28, wherein the x-ray source assembly further comprises means for generating electrons, and means for impinging the electrons onto one of the plurality of the target materials.

30. The system of claim 29, wherein the means for impinging comprises an electromagnetic field generator for deflecting the electrons such that they impinge onto the one of the plurality of the target materials.

31. The system of claim 24, wherein the first set of image data comprises data sufficient for generating a volumetric image.

32. The system of claim 24, wherein the first set of image data comprises a plurality of image frames generated by placing a radiation source in different orientations.

33. The system of claim 24, wherein the means for generating the first set of image data comprises a detector and a positioner for placing the detector in different positions.

34. The system of claim 24, wherein the means for creating the volumetric composite image is configured to determine a first volumetric image from the first set of image, determine a second volumetric image from the second set of image, and subtract the first volumetric image from the second volumetric image.

35. The system of claim 24, wherein the means for creating the volumetric composite image is configured to create the volumetric composite image by obtaining a set of composite images using the first and second sets of image data, the set of composite images being two-dimensional images, and constructing the volumetric composite image using the set of composite images.

36. A non-transitory computer readable medium having a set of stored instructions, the execution of which causes a process to be performed, the process comprising:
   generating a first set of image data for a bodily region that includes a contrast agent using radiation at a first energy level;
   generating a second set of image data for the bodily region that includes the contrast agent using radiation at a second energy level;
   creating a contrast-enhanced volumetric composite image using the first and the second sets of image data, wherein the contrast-enhanced volumetric composite image is created such that at least a portion of the contrast-enhanced volumetric composite image has a feature indicating cancerous tissue, and that an image contrast for bone and tissue that does not contain the contrast agent at another portion of the contrast-enhanced volumetric composite image is reduced;
   at least one of storing the contrast-enhanced volumetric composite image and displaying the contrast-enhanced volumetric composite image;
   determining information regarding time-resolved kinetics of the contrast agent in the body based at least in part on the volumetric composite image;
   providing a first graphic that indicates the determined information; and
   providing a second graphic that indicates time-resolved kinetics of a contrast agent in normal tissue, the contrast agent in the normal tissue being a same type as the contrast agent in the body;
   wherein the first and second graphics are provided in a same graph for comparison.

37. The computer product of claim 36, wherein the first energy level is below a k-edge of a contrast agent.

38. The computer product of claim 36, wherein the second energy level is above a k-edge of a contrast agent.

39. The computer product of claim 36, wherein the first and the second sets of image data are generated by performing a computed tomography procedure.

40. The computer product of claim 36, wherein the computed tomography procedure is performed using a cone beam.

41. The computer product of claim 36, wherein the first and the second sets of image data are generated by performing a MRI procedure.

42. The computer product of claim 36, wherein the first and the second sets of image data are generated by performing a PET procedure.

43. The computer product of claim 36, wherein the volumetric composite image is created by subtracting the first set of image data from the second set of image data.

44. The computer product of claim 36, wherein the volumetric composite image is created by modifying the first set of image data; modifying the second set of image data; and subtracting the first modified set of image data from the second modified set of image data.

45. The computer product of claim 44, wherein the acts of modifying comprises applying a logarithmic transform to the first and the second sets of image data.

46. The computer product of claim 36, wherein the first and the second sets of image data are generated within 5 to 20 microseconds.

47. The computer product of claim 36, wherein the radiation at either or both of the first and the second energy levels are generated using a multi-energy x-ray source assembly.

48. The computer product of claim 36, wherein the volumetric composite image is created by removing a tissue feature, and retaining a feature attributable to the contrast agent.

49. The computer product of claim 36, wherein the radiation at the first and the second energy levels are generated by switching a x-ray tube voltage between a first and a second levels.

50. The computer product of claim 36, wherein the radiation at the first and the second energy levels are generated by impinging an electron beam onto a first target material and a second target material, respectively.

51. The computer product of claim 36, wherein the radiation at the first and the second energy levels are generated by filtering x-rays through a first filter and a second filter, respectively.

52. The computer product of claim 36, wherein the volumetric composite image is created by determining a first volumetric image from the first set of image, determining a second volumetric image from the second set of image, and subtracting the first volumetric image from the second volumetric image.

53. The computer product of claim 36, wherein the volumetric composite image is created by obtaining a set of composite images using the first and second sets of image data, the set of composite images being two-dimensional images, and constructing the volumetric composite image using the set of composite images.

54. A method of generating one or more images of a portion of a body, comprising:
introducing a contrast agent into the body;
generating a first set of image data using radiation at a first energy level after the contrast agent is introduced into the body;
generating a second set of image data using radiation at a second energy level after the contrast agent is introduced into the body;
creating a contrast-enhanced volumetric composite image using the first and the second sets of image data, wherein the contrast-enhanced volumetric composite image is created such that at least a portion of the contrast-enhanced volumetric composite image has a feature indicating cancerous tissue, and that an image contrast for bone and tissue that does not contain the contrast agent at another portion of the contrast-enhanced volumetric composite image is reduced; and
at least one of storing the contrast-enhanced volumetric composite image and displaying the contrast-enhanced volumetric composite image;
wherein the first and the second sets of image data are generated using one imager, the imager having a first line, a second line, a third line, and a fourth line of image elements; and
wherein the generating the first and the second sets of image data comprises:
deactivating the first and the third lines of the image elements and activating the second and the fourth lines of the image elements while applying the radiation at the first energy level; and
activating the first, the second, the third, and the fourth lines of the image elements while applying the radiation at the second energy level.

55. A non-transitory computer readable medium computer product having a set of stored instructions, the execution of which causes a process to be performed, the process comprising:
generating a first set of image data for a bodily region that includes a contrast agent using radiation at a first energy level;
generating a second set of image data for the bodily region that includes the contrast agent using radiation at a second energy level;
creating a contrast-enhanced volumetric composite image using the first and the second sets of image data, wherein the contrast-enhanced volumetric composite image is created such that at least a portion of the contrast-enhanced volumetric composite image has a feature indicating cancerous tissue, and that an image contrast for bone and tissue that does not contain the contrast agent at another portion of the contrast-enhanced volumetric composite image is reduced; and
at least one of storing the contrast-enhanced volumetric composite image and displaying the contrast-enhanced volumetric composite image;
wherein the first and the second sets of image data are generated using one imager, the imager having a first line, a second line, a third line, and a fourth line of image elements; and
wherein the generating the first and the second sets of image data comprises:
deactivating the first and the third lines of the image elements and activating the second and the fourth lines of the image elements while applying the radiation at the first energy level; and
activating the first, the second, the third, and the fourth lines of the image elements while applying the radiation at the second energy level.

56. A system of generating one or more images of a portion of a body after a contrast agent is introduced into the body, the system comprising:
means for generating a first set of image data using radiation at a first energy level after the contrast agent is introduced into the body;
means for generating a second set of image data using radiation at a second energy level after the contrast agent is introduced into the body, wherein the first energy level is below a k-edge of the contrast agent, and the second energy level is above a k-edge of the contrast agent; and means for creating a contrast-enhanced volumetric composite image using the first and the second sets of image data, wherein the means for creating is configured to create the contrast-enhanced volumetric composite image such that at least a portion of the contrast-enhanced volumetric composite image has a feature indicating cancerous tissue, and that an image contrast for bone and tissue that does not contain the contrast agent at another portion of the contrast-enhanced volumetric composite image is reduced;

wherein the means for generating the first set of image data and the second set of image data comprises an imager having a first line of image elements, a second line of image elements, a third line of image elements, and a fourth line of image elements; and wherein the imager is configured to deactivate the first and the third lines of the image elements and activate the second and the fourth lines of the image elements while applying the radiation at the first energy level, and activate the first, the second, the third, and the fourth lines of the image elements while applying the radiation at the second energy level.

* * * * *